(12) United States Patent  (10) Patent No.: US 7,954,688 B2
Argentine et al.  (45) Date of Patent: Jun. 7, 2011

(54) ENDOVASCULAR STAPLING APPARATUS AND METHODS OF USE

(75) Inventors: Jeff Argentine, Petaluma, CA (US); Jeff Sandstrom, Forest Lake, MN (US); Damian Jelich, Cottage Grove, MN (US); Eric Meyer, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 258 days.

(21) Appl. No.: 12/424,261

(22) Filed: Apr. 15, 2009

(65) Prior Publication Data

US 2010/0044410 A1    Feb. 25, 2010

Related U.S. Application Data

(60) Provisional application No. 61/091,219, filed on Aug. 22, 2008.

(51) Int. Cl.
*A61B 17/068* (2006.01)

(52) U.S. Cl. .............. 227/176.1; 227/19; 227/175.1; 606/153; 606/219

(58) Field of Classification Search .............. 227/19, 227/176.1, 175.1, 180.1, 179.1; 606/139, 606/153, 219, 151
See application file for complete search history.

(56) References Cited

U.S. PATENT DOCUMENTS

| | | | | |
|---|---|---|---|---|
| 4,595,007 A * | 6/1986 | Mericle | ................... | 606/221 |
| 5,002,563 A | 3/1991 | Pyka et al. | | |
| 5,217,027 A * | 6/1993 | Hermens | ................... | 607/126 |
| 5,554,162 A * | 9/1996 | DeLange | ................... | 606/153 |
| 5,695,504 A * | 12/1997 | Gifford et al. | ................... | 606/153 |
| 5,715,987 A * | 2/1998 | Kelley et al. | ................... | 227/175.1 |
| 5,725,554 A * | 3/1998 | Simon et al. | ................... | 606/219 |
| 5,871,528 A * | 2/1999 | Camps et al. | ................... | 607/119 |
| 6,007,563 A * | 12/1999 | Nash et al. | ................... | 606/213 |
| 6,149,660 A * | 11/2000 | Laufer et al. | ................... | 606/143 |
| 6,165,183 A * | 12/2000 | Kuehn et al. | ................... | 606/139 |
| 6,221,083 B1* | 4/2001 | Mayer | ................... | 606/139 |
| 6,776,784 B2 | 8/2004 | Ginn | | |
| 6,926,730 B1 | 8/2005 | Nguyen et al. | | |
| 7,004,958 B2* | 2/2006 | Adams et al. | ................... | 606/219 |
| 7,335,212 B2 | 2/2008 | Edoga et al. | | |
| 7,338,503 B2* | 3/2008 | Rosenberg et al. | ................... | 606/142 |
| 7,399,310 B2 | 7/2008 | Edoga et al. | | |
| 2001/0018592 A1 | 8/2001 | Schaller et al. | | |
| 2005/0004582 A1 | 1/2005 | Edoga et al. | | |
| 2006/0253143 A1 | 11/2006 | Edoga et al. | | |
| 2007/0162053 A1 | 7/2007 | Jones et al. | | |

* cited by examiner

*Primary Examiner* — Scott A. Smith

(57) ABSTRACT

An endovascular stapling apparatus for delivering a staple to a vessel of a patient, including a plurality of clips, a housing, and a rod. Each of the clips includes a bridge and legs that self-transition from a biased state to a natural state in which the legs each form a loop. The housing defines a channel and a window open to the channel. The clips are retained within the channel in the biased state. The rod is slidably disposed within the channel, selectively moves the clips toward and away from the window, and releases the clips from the window.

31 Claims, 23 Drawing Sheets

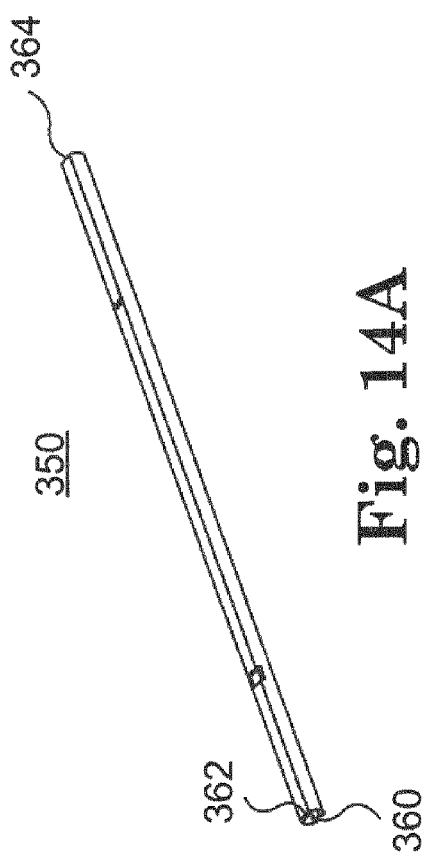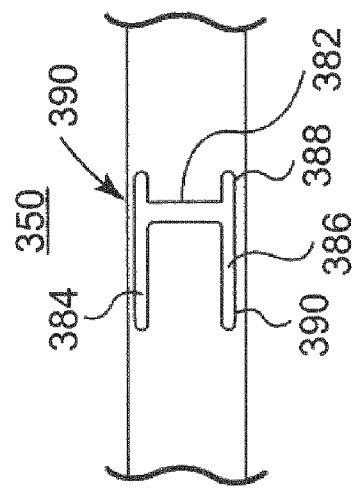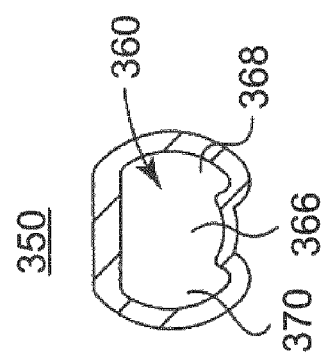

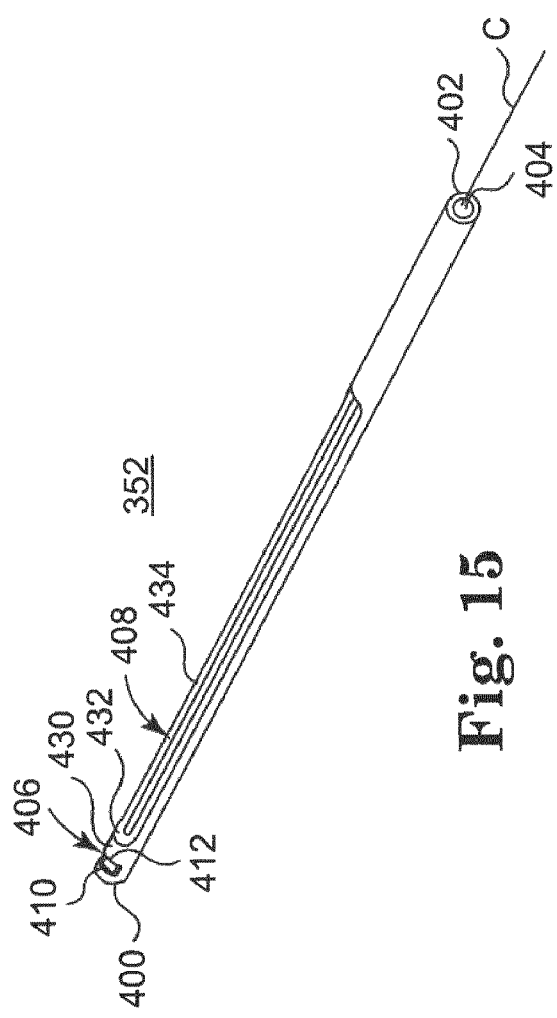
Fig. 15
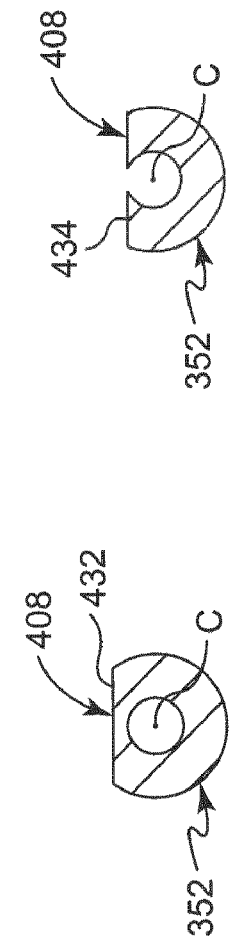
Fig. 16B
Fig. 16C
Fig. 16A

ENDOVASCULAR STAPLING APPARATUS AND METHODS OF USE

CROSS-REFERENCE TO RELATED APPLICATION

This application claims priority under 35 U.S.C. §119(e)(1) to U.S. Provisional Patent Application Ser. No. 61/091,219, filed Aug. 25, 2008 entitled "Endovascular Stapling Apparatus and Methods of Use", and bearing; and the entire teachings of which are incorporated herein by reference.

BACKGROUND

The present disclosure generally relates to endostapler delivery systems and methods employed in the treatment of vascular disease. More particularly, it relates to endovascular stapling devices and methods for use in the fixation of grafts to the walls of vessels.

In modern medical practice, it is sometimes desirable to pass a staple or clip into or through the wall of a luminal anatomical structure (e.g., a blood vessel or other anatomical conduit) for the purpose of attaching an article (e.g., an endoluminal, extraluminal or transluminal graft) or other apparatus to the wall of the anatomical structure.

Examples of medical procedures wherein it is desirable to anchor or attach a graft or other apparatus to the wall of a blood vessel or other luminal anatomical conduit includes certain endovascular grafting procedures whereby a tubular graft is placed within the lumen of an aneurysmic blood vessel to create a neo-lumen or artificial flow conduit through an aneurism, thereby eliminating the exertion of blood pressure on the aneurism and allowing the aneurysmic space to subsequently become filled in with granulation tissue. These endovascular grafting procedures have heretofore been used to treat aneurisms of the abdominal aorta, as well as aneurisms of the descending thoracic aorta. The endovascular grafts typically incorporate or are combined with one or more radially expandable stents which are radially expanded in situ to anchor the tubular graft to the wall of the blood vessel at sites upstream and downstream of the aneurism. Thus, the grafts are typically held in place by friction via the self-expanding or balloon expandable stents. The grafts may also be affixed to vessels with hooks or barbs.

However, in the event that these stent(s) fail to establish sound frictional engagement with the blood vessel wall, the graft may undergo undesirable migration or slippage, or blood may leak into the aneurysmic sac (sometimes referred to as an "endoleak"). Thus, in view of the above-mentioned undesirable complications associated with the use of radially expandable stents to frictionally anchor a graft or other apparatus to the wall of a blood vessel (or other luminal anatomical structure), there exists a need for the development of new endoluminal attachment devices which may be used to deliver one or more staples in attaching the opposite end of an endoluminal tube graft (or other article) to the surrounding wall of the blood vessel or tubular anatomical conduit, thereby ensuring sound and permanent placement of the graft or other article. In this regard, while surgical stapling devices are generally known, the anatomical constraints presented by endovascular application (e.g., catheter-based) present numerous staple/clip deployment difficulties.

SUMMARY

Some aspects in accordance with principles of the present disclosure relate to an endovascular stapling apparatus for delivering a staple to a vessel of a patient. The apparatus includes a plurality of clips, an elongate clip deployment housing, and a deployment rod. Each of the clips includes a bridge interconnecting opposing legs. The clips are configured to self-transition from a biased state in which the legs are relatively straight to a natural state in which the legs each form a loop. The housing defines a channel, and forms a deployment window open to the channel. In this regard, the plurality of clips are retained within the channel in the biased state. The deployment rod is slidably disposed within the channel, and is configured to interface with the clips. More particularly, the deployment rod is configured to selectively move the clips toward and away from the deployment window in response to a corresponding, user-applied force such that the clips are consecutively releasable from the deployment window with movement of the deployment rod. In some embodiments, in a loaded state, each of the clips are maintained within the housing distal the deployment window, with proximal movement of the deployment rod relative to the housing effectuating consecutive delivery of each of the clips. In other embodiments, the deployment rod is configured to capture selective ones of the clips for subsequent deployment through the deployment window, with the clips not otherwise captured by the deployment rod remaining stationary relative to the housing with sliding movement of the deployment rod. Regardless, in some embodiments, the deployment rod forms a notch sized to selectively capture the bridge of one of the clips, with the so-captured clip moving proximally and distally relative to the deployment housing with corresponding, proximal and distal movement of the deployment rod.

Other aspects in accordance with principles of the present disclosure relate to a method of delivering a staple through a bodily lumen. The method includes providing an endovascular stapling apparatus including a plurality of clips, a delivery assembly, and a catheter. The delivery assembly includes a housing slidably maintaining a deployment rod. The clips each include a bridge interconnecting opposing legs, and are retained within a channel of the housing in a biased state in which the legs are relatively straight. The housing further forms a deployment window that is open to the channel, with the deployment rod slidably disposed within the channel and configured to selectively interface with the clips. Finally, the housing is disposed within a lumen of the catheter. With this in mind, the deployment window is positioned at a target site of the bodily lumen via the catheter. The deployment rod is proximally retracted relative to the housing to deploy an exposed portion of the first clip from the window. The position of the partially deployed clip relative to the bodily lumen is evaluated, and the deployment rod distally advanced relative to the housing to at least partially withdraw the exposed portion of the first clip back into the housing. The deployment window is then repositioned relative to the bodily lumen, and the deployment rod proximally retracted relative to the housing to fully deploy the first clip. In some embodiments, the method includes repeatedly partially deploying the first clip from, and withdrawing the first clip back into, the deployment window via proximal and distal movement of the deployment rod. In other embodiments, a second clip is deployed from the deployment window via further proximal retraction of the deployment rod relative to the deployment housing. In yet other embodiments, deployment of a second clip includes proximally retracting the deployment rod to capture the bridge of the second clip, distally advancing the deployment rod to position the bridge distally beyond the deployment window, and then proximally retracting the deployment rod to deploy the second clip from the deployment window.

BRIEF DESCRIPTION OF THE DRAWINGS

FIG. 14A is a perspective view of a housing component useful with a delivery assembly portion of the apparatus of FIG. 12;

FIG. 14B is a cross-sectional view of the housing of FIG. 14A;

FIG. 14C is an enlarged, top view of a portion of the housing of FIG. 14A;

FIG. 15 is an enlarged, perspective view of a deployment rod component of the delivery assembly portion of the apparatus of FIG. 12;

FIGS. 16A-16C are cross-sectional views of portions of the deployment rod of FIG. 15;

DETAILED DESCRIPTION

Figure 1:
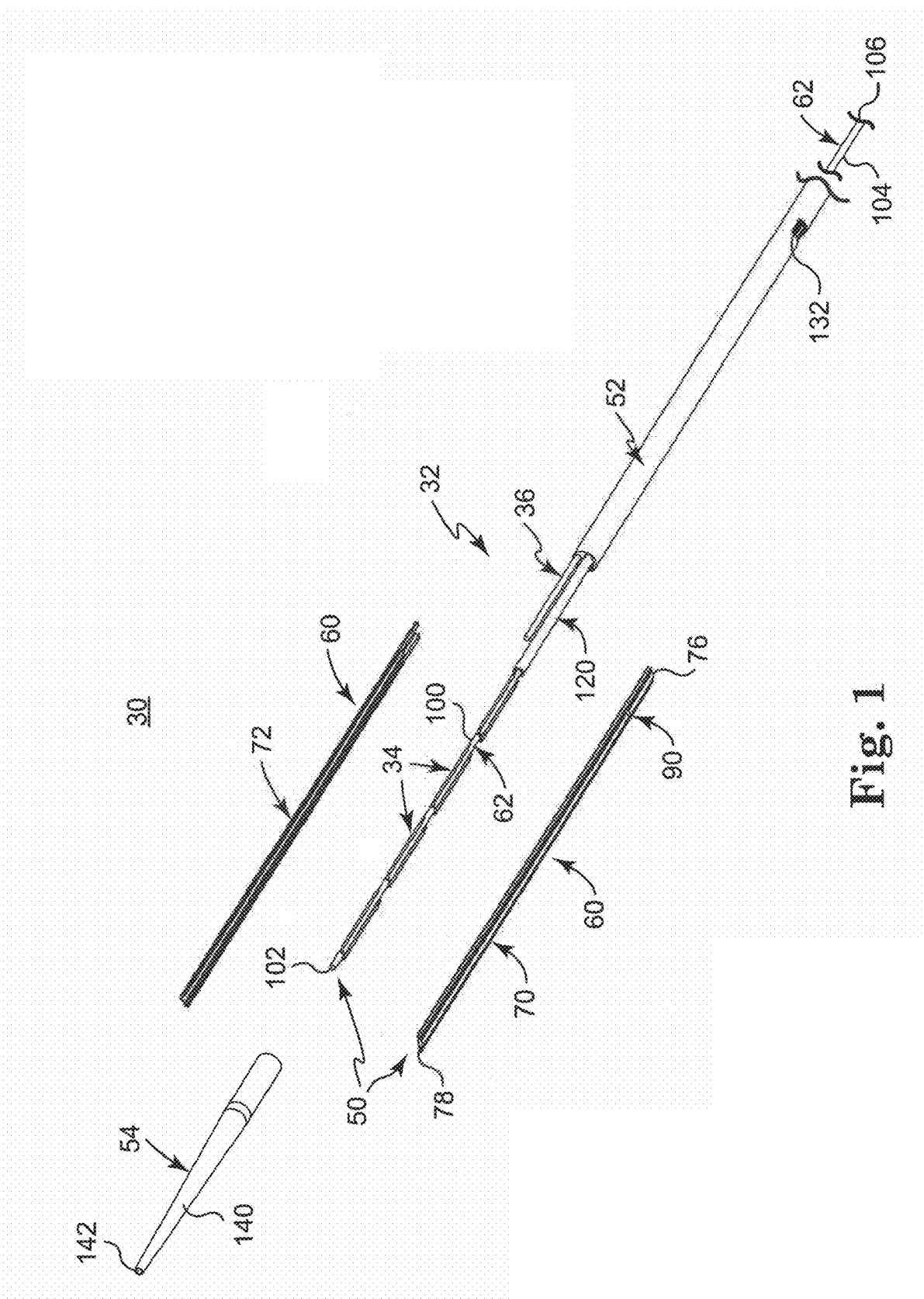
FIG. 1 is an exploded view of an endovascular stapling apparatus in accordance with principles of the present disclosure.

Portions of one configuration of an endovascular stapling apparatus 30 in accordance with aspects of the present disclosure are shown in FIG. 1. The apparatus 30 includes a delivery instrument 32 (referenced generally) maintaining a plurality of self-closing clips 34. Details on the various components are provided below. In general terms, however, the delivery instrument 32 maintains the clips 34 in a biased state (reflected in FIG. 1), and is operable to selectively deploy ones of the clips 34 therefrom. An optional guide wire 36 component of the apparatus 30 facilitates desired placement of the instrument 32 (e.g., aortic and iliac arterial use). Similarly, an optional biasing device (not shown) operates to offset or counter forces generated by use of the delivery instrument 32, as well as to facilitate delivery of the clips 34 at desired locations relative to a vessel wall and/or graft. Regardless, the delivery instrument 32 provides the treating clinician with the ability to partially deploy and retract the clips 34 during use. Although the present disclosure is in the context of treatment of blood vessels such as the aorta and coronary, carotid, and renal arteries, principles of the present disclosure may also be used in any other body passageways where it is deemed useful.

As a point of reference, certain features of the delivery instrument 32 are more readily described in the context of various aspects associated with the clips 34. With this in mind, each of the clips 34 is transitionable from a natural or undeformed state to the biased state reflected in FIG. 1, and self-revert back to the natural or undeformed state. In this regard, operation of the delivery instrument 32 in retaining and subsequently deploying or releasing the clips 34 is, in some embodiments, premised upon a shape memory attribute of the clips 34. With additional reference to FIG. 2 (that otherwise illustrates one non-limiting example of one of the clips 34 in the natural or undeformed state), the clip 34 exhibits a loop-shaped memory set shape or configuration. For example, the clip 34 includes a bridge 40 interconnecting opposing legs 42, 44. In the natural undeformed state of FIG. 2, each of the legs 42, 44 forms an overlapping loop, although in other embodiments, the loop-like shape can be non-overlapping. The clip 34 can be Nitinol wire and provided with the desired memory set configuration to exhibit pseudo elastic (super elastic) behavior. In other words, at least a portion of the shape memory alloy is converted from its austenitic phase to its martensitic phase when the wire is in its deformed configuration. As the stress is removed, the material undergoes a martensitic to austenitic conversion and springs back (e.g., self-reverts) to its original or undeformed or undeflected configuration. Regardless, each of the legs 42, 44 terminate at an end 46, 48, respectively, opposite the bridge 40 that are, in some embodiments, sharpened to promote piercing of target tissue (not shown). Alternatively, one or both of the end(s) 46 and/or 48 can be blunt. Additional examples of clips useful with the present disclosure are described in U.S. Pat. No. 6,926,730 entitled "Minimally Invasive Valve Repair Procedure and Apparatus"; U.S. application Ser. No. 09/828,322 filed Apr. 5, 2001 and entitled "Bridge Clip Tissue Connector Apparatus and Methods"; and U.S. Provisional Application Ser. No. 61/035,245 filed Mar. 10, 2008 and entitled "Apparatus and Methods for Minimally Invasive Valve Repair"; an entirety of the teachings of each of which are incorporated herein by reference.

Returning to FIG. 1 and with the above parameters of the clips 34 in mind, the delivery instrument 32 includes several components, such as a delivery assembly 50, a catheter 52, an actuator or handle (not shown), an introducer 54, and the optional biasing device (not shown). The delivery assembly 50 maintains and deploys the clips 34 via operation of the actuator, with the catheter 52 serving to couple various components, such as the biasing device and the guide wire 36 to the delivery assembly 50. The introducer 54 promotes atruamatic arterial delivery of the instrument 32.

The delivery assembly 50 includes, in some constructions, a housing 60 and a; deployment rod 62. In general terms, the deployment rod 62 is slidably disposed within the housing 60, and is adapted to interface with the clips 34 as described below. Further, the housing 60 is adapted to retain the clips 34 in a biased state, and permit deployment of the clips 34 therefrom. Though not shown, the movement of the deployment rod 64 relative to the housing 60 is effectuated by the actuator that otherwise connected to a proximal region of the deployment rod 62.

Figure 2:
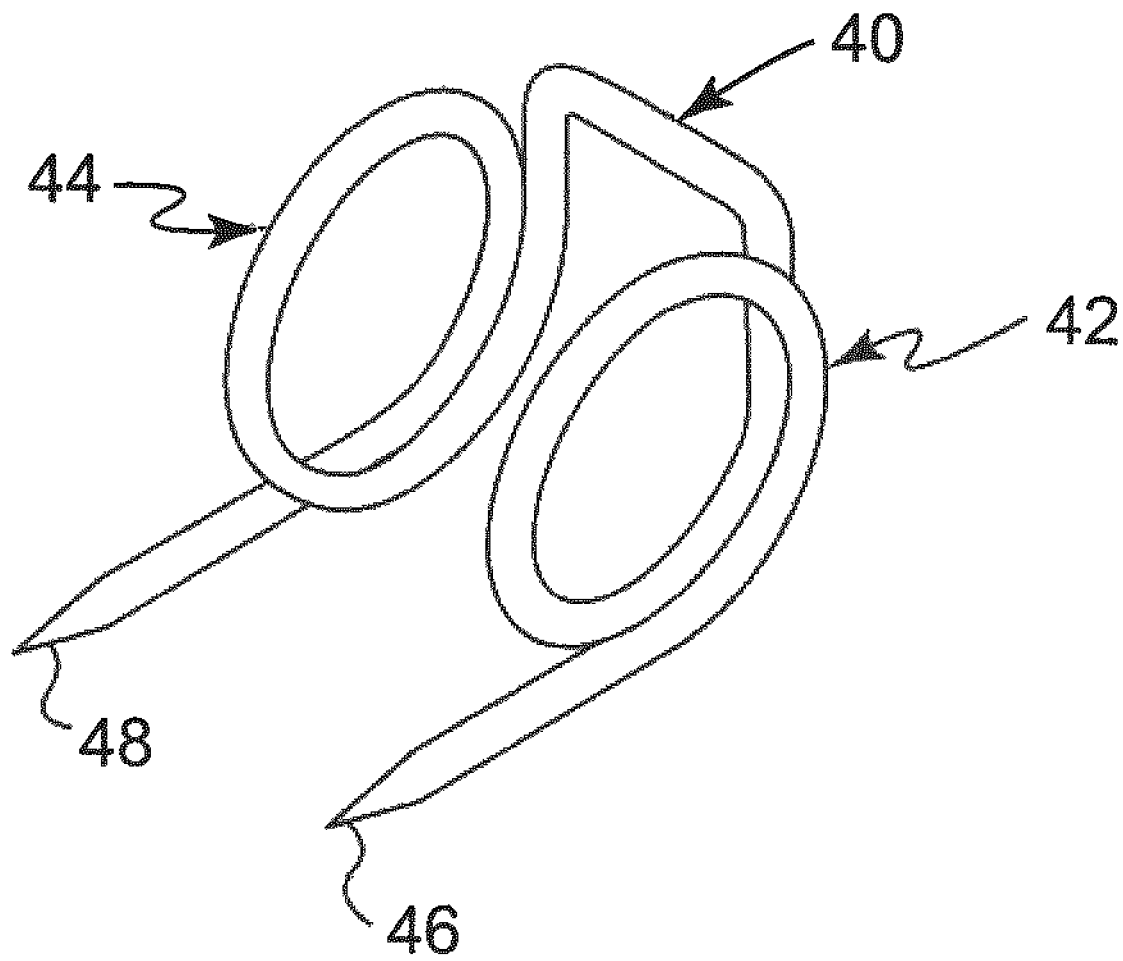
FIG. 2 is an enlarged, perspective view of a self-closing clip useful with the apparatus of FIG. 1.
Figure 3:
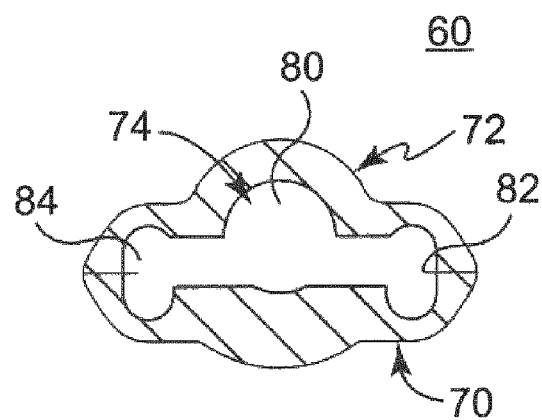
FIG. 3 is an enlarged view of a housing component of a delivery assembly portion of the apparatus of FIG. 1.

With additional reference to FIG. 3, the housing 60 generally elongated, and can be formed by first and second housing sections 70, 72 (best shown in FIG. 1). Alternatively, the housing 60 can be formed as a homogeneous body (e.g., an extruded tube), or can consist of three or more components assembled to one another. Regardless, the housing 60 forms an internal channel 74 extending between, and open relative to, proximal and distal ends 76, 78 of the housing 60 (identified for the first housing section 70 in FIG. 1). With specific reference to FIG. 3, the channel 74 includes or is defined by, in some embodiments, a central segment 80 and opposing side segments 82, 84. The segments 80-84 are open relative to one another, and are sized in accordance with the deployment rod 62 (FIG. 1) and the clips 34 (FIG. 1). For example, the central segment 80 is generally circular in transverse cross-section, defining a diameter commensurate with (e.g., slightly greater than) a corresponding diameter of the deployment rod 62. The side segment 82, 84 are generally identical in shape, and are configured to slidably maintain corresponding legs 42, 44 (FIG. 2) of the clips 34 in a manner that forces the legs 42, 44 to a desired shape.

Figure 4A:
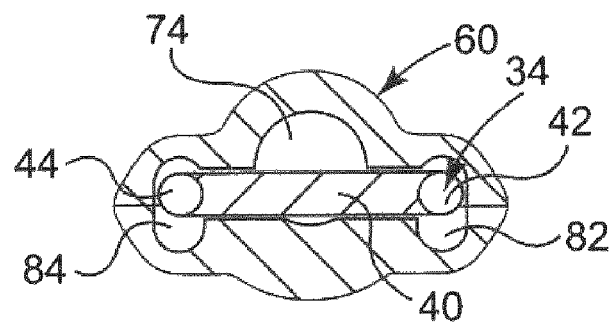
FIG. 4A is an enlarged view of a portion of the housing of FIG. 3.
Figure 4B:
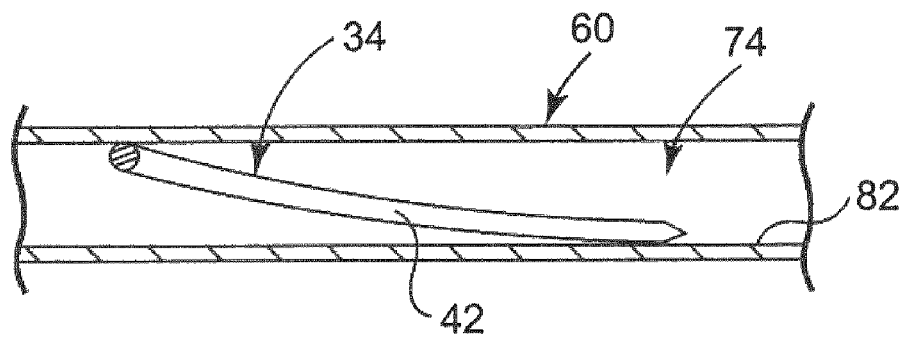
FIG. 4B is a cross-sectional illustration of the housing of FIG. 4A with a clip disposed therein.

More particularly and with additional reference to FIG. 2, the channel 74 is sized and shaped to force or bias the legs 42, 44 of each of the clips 34 to a deformed, generally straightened state in which the legs 42, 44 do not form a loop. Once again, FIG. 1 generally reflects the clips 34 in this biased, generally straightened state (it being understood that the legs 42, 44 need not be truly straight or "non-curved" in the deformed state dictated by the housing 62). Thus, for example, a width of the channel 74 (e.g., distance between the side segments 82, 84) is commensurate with a length of the bridge 40 as shown in FIG. 4A. Similarly, the side segments 82, 84 are sized to receive a corresponding one of the legs 42, 44 with the side segments 82, 84 having a height that allows the corresponding leg 42 or 44 disposed therein to assume some curvature in longitudinal extension, but to otherwise be maintained in a relatively straight state as shown in FIG. 4B.

Figure 5:
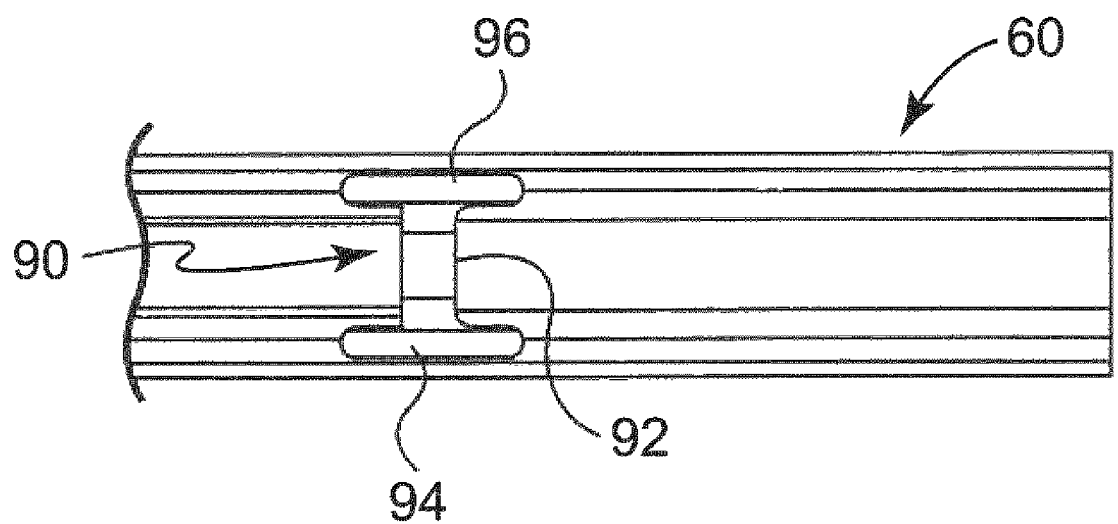
FIG. 5 is an enlarged view of a portion of the housing of FIG. 3.

Returning to FIG. 1, a length of the housing 60 is selected to accommodate a desired number of the clips 34 (in the deformed, relatively straight state), with the clips 34 arranged end-to-end (i.e., the longitudinal arrangement of the clips 34 as shown in FIG. 1). In some embodiments, then, the housing 60 is sized to retain four of the clips 34, although in other embodiments, any other number of the clips 34 can be accommodated. Regardless, the housing 60 forms a deployment window 90 through a side wall thereof, and open to the internal channel 74 (FIG. 3). The deployment window 90 is generally sized and shaped to permit release or deployment of one of the clips 34 from the channel 74. For example, FIG. 5 illustrates one embodiment of the deployment window 90 in greater detail, including or defining a central portion 92 and opposing end portions 94, 96. The central portion 92 is sized and shaped in accordance with the bridge 40 (FIG. 2) of the clip 34, whereas the end portions 94, 96 are sized to permit passage of a respective one of the legs 42 or 44 (FIG. 2). In some constructions, the end portions 94, 96 are slightly elongated (i.e., extend longitudinally proximal and distal the central portion 92) to better assist in deployment and retraction of the legs 42, 44 relative to the deployment window 90. Alternatively, the deployment window 90 can assume a wide variety of other shapes and/or sizes.

In order to constrain the clips 34 in the biased or deformed state as described above while still permitting arterial delivery, the housing 60 is formed of a semi-flexible yet hardened material, such as PEEK. With this construction, the housing 60 prevents forces of the constrained clips 34 from deforming and/or puncturing through the housing 60 (as well as the catheter 52) during use.

As shown in FIG. 1, the deployment rod 62 is an elongated body defining a distal segment 100 terminating at a distal end 102, and a proximal segment 104 terminating at a proximal end 106. The deployment rod 62 has a longitudinal length greater than a longitudinal length of the housing 60. More particularly, the deployment rod 62 is sized such that upon final assembly, the distal segment 100 resides within the housing 60, whereas the proximal segment 104 extends proximally therefrom (as well as proximally beyond the catheter 52). Though not illustrated, the proximal segment 104 is configured for attachment to the actuator (e.g., a handle) by which a user can effectuate sliding movement of the deployment rod 62 relative to the housing 60, including proximally retracting the deployment rod 62 relative to the housing 60 as well as distally advancing the deployment rod 62 relative to the housing 60. For example, the actuator can include handle members pivotably connected to one another, with one of the handle members connected to the deployment rod 62.

Figure 6A:
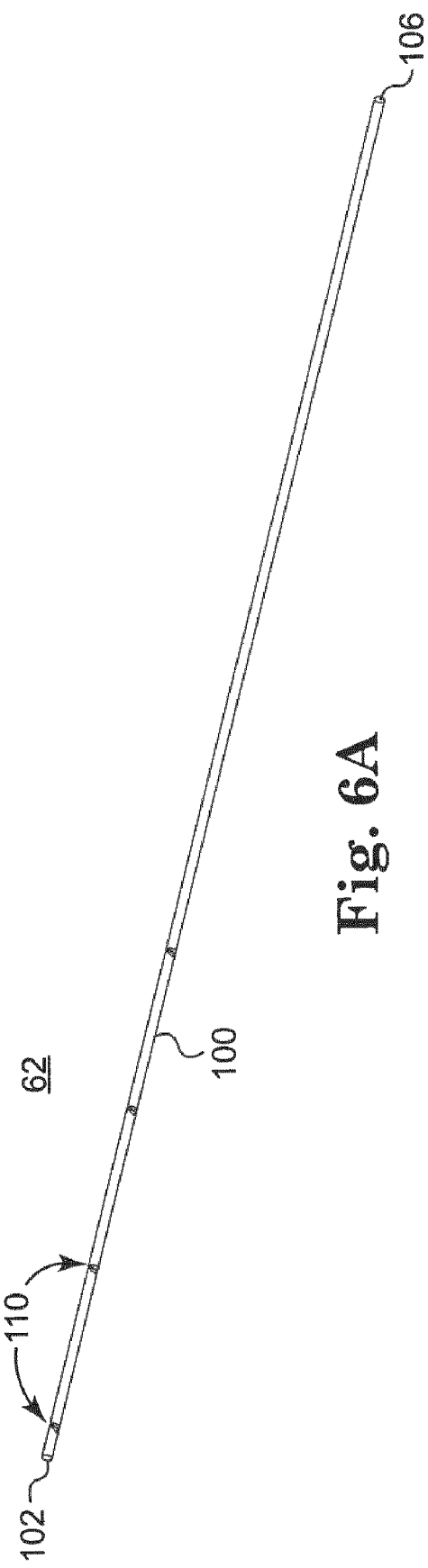
FIG. 6A is an enlarged, perspective view of a deployment rod component of a delivery assembly portion of the apparatus of FIG. 1.
Figure 6B:
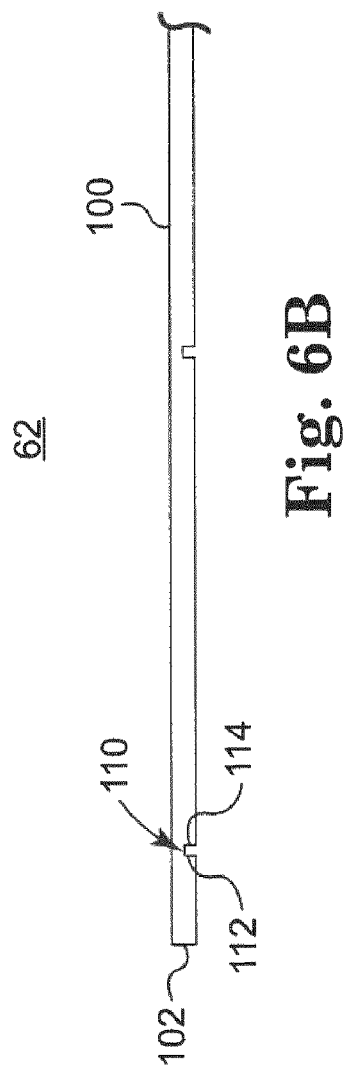
FIG. 6B is an enlarged side view of a portion of the deployment rod of FIG. 6A.

As described above, the deployment rod 62 is sized to be slidably disposed within the channel 74 (FIG. 3) of the housing 60. Further, the deployment rod 62, and in particular the distal segment 100, is configured to interface with the clips 34. For example, a diameter (or other outer dimension) of the deployment rod 62 is less than a length of the bridge 40 (FIG. 2) of each of the clips 34 such that upon final assembly, the legs 42, 44 (FIG. 2) are positionable at opposite sides of the deployment rod 62. In other words, a diameter of the deployment rod 62 is less than a lateral spacing between the legs 42, 44. Also, and with reference to FIGS. 6A and 6B, the distal segment 100 forms one or more notches 110 each sized to selectively receive or capture a respective one of the clips 34. In general terms, each of the notches 110 is formed or defined by a distal side wall or surface 112 and a proximal side wall or surface 114 that combine to define a width of the notch 110. The notch width is commensurate with a diameter (or other outer major dimension) of the bridge 50 (FIG. 2) of the clips 34, such that the bridge 40 can be received or partially captured within the notch 110. In this regard, each of the walls 112, 114 are configured to impart or transfer a sliding force from the deployment rod 62 onto the so-received clip 34. For example, a retraction force applied to the deployment rod 62 (i.e., a force in the proximal direction) is imparted onto the corresponding clip 34 via the distal wall 112; similarly, distal movement of the deployment rod 62 is transferred onto the clip 34 via the proximal wall 114. Notably, however, in the absence of external constraining forces (i.e., the housing 60), a relationship between the size of the notch 110 and of the bridge 40 is such that the clip 34 is freely releasable from the notch 110.

As indicated above, in some embodiments, the delivery assembly 50 is configured to initially retain four of the clips 34 as shown in FIG. 1. Under these constructions, the distal segment 100 forms four of the notches 110. Thus, where fewer or more of the clips 34 are provided with the apparatus 30, a corresponding greater or lesser number of the notches 110 can also be incorporated. In yet other embodiments, the delivery assembly 50 can be constructed such that the deployment rod 62 interfaces with the clips 34 on an individual basis, such that only one of the notches 110 is provided.

As with many other components of the stapling apparatus 30, the deployment rod 62 is constructed to be at least semi-flexible, and thus amenable to arterial delivery techniques. However, the deployment rod 62 exhibits longitudinal rigidity or hardness sufficient for transferring forces onto the clips 34, in moving the clips 34 within the housing 60. In some embodiments, then, the deployment rod 62 is formed of a Nitinol material, although other materials can be employed. Further, some embodiments of the delivery assembly 50 incorporate an axial support tube 120. The deployment rod 62 is coaxially disposed within the support tube 120, with the support tube 120 enhancing a longitudinal rigidity of the deployment rod 62. Where provided, the support tube 120 terminates proximal the distal segment 100 of the deployment rod 62 so as to not interfere with desired placement/location of the clips 34.

Figure 7:
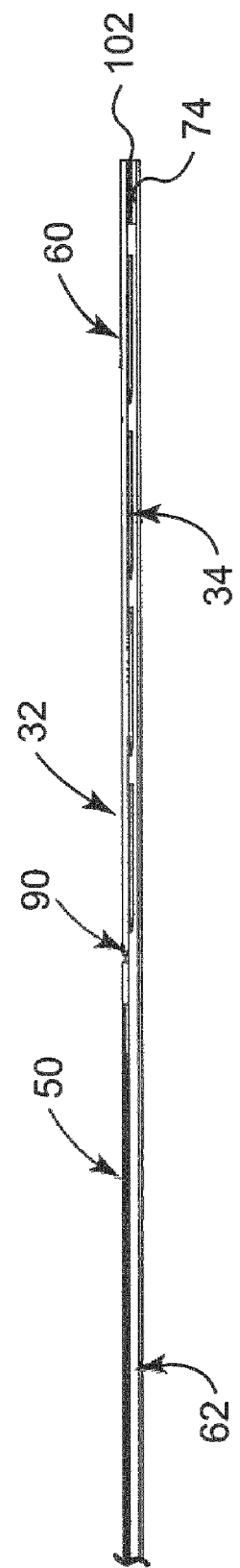
FIG. 7 is a perspective view of the apparatus of FIG. 1 upon final assembly.

Upon final construction of the delivery assembly 50 (including the clips 34) in an initial state (i.e., prior to deployment of any of the clips 34), the deployment rod 62 and the clips 34 are disposed within the channel 74 of the housing 60 as shown in FIG. 7. Once again, the deployment rod 62, as well as the clips 34 are slidable relative to the housing 60 along the channel 74. More particularly, the clips 34 are longitudinally movable relative to the housing 60 with sliding movement of the deployment rod 62. With the one configuration of FIG. 7, in the initial state, each of the clips 34 are positioned distal the deployment window 90 of the housing 60. As described below, then, deployment of the clips 34 from the housing 60 (via the deployment window 90) generally entails proximally retracting the deployment rod 62 relative to the housing 60.

Figure 8:
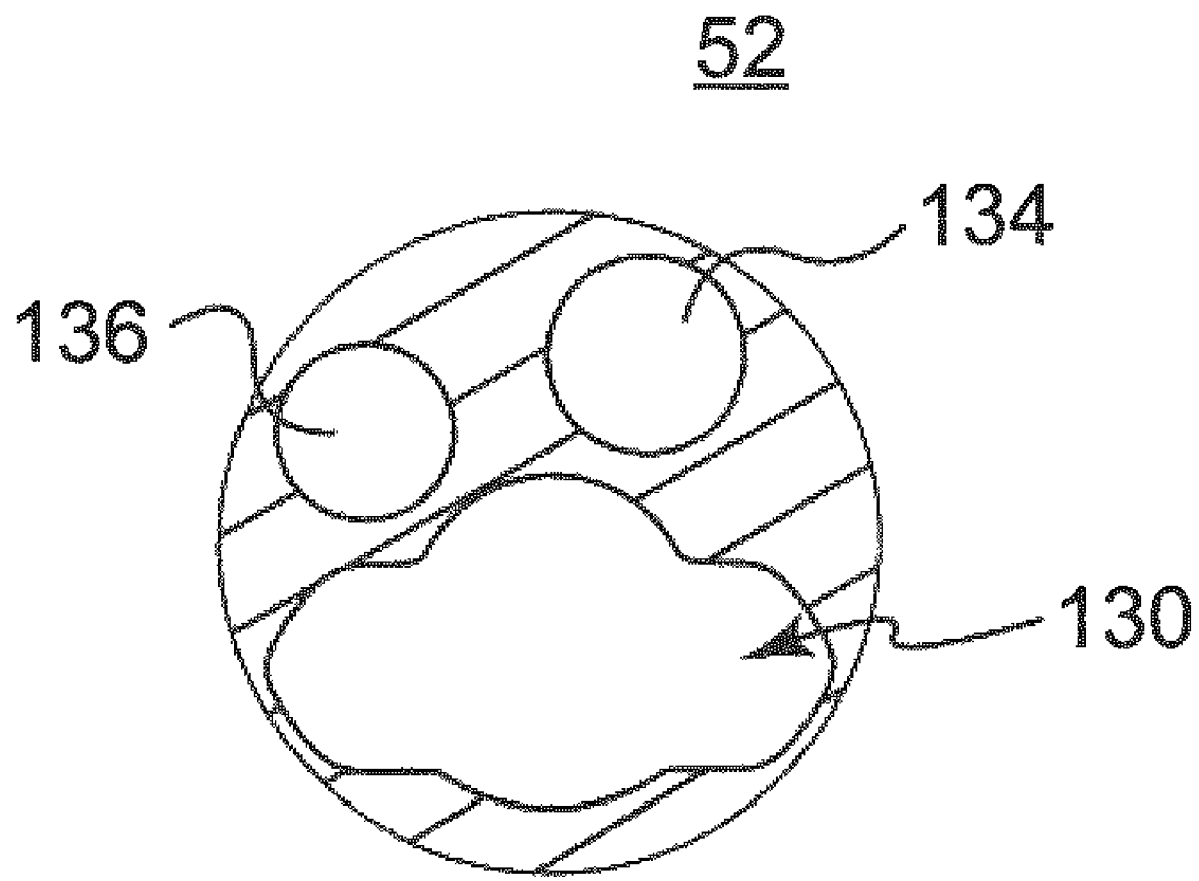
FIG. 8 is a cross-sectional view of a catheter portion of the apparatus of FIG. 1.

Returning to FIG. 1, the catheter 52 can be formed of various materials appropriate for arterial delivery (e.g., extruded catheter having a profile or outer diameter of approximately 4 mm-5 mm (12-15 French units)), and is sized to receive the delivery assembly 50. In this regard, and with additional reference to FIG. 8, the catheter 52 forms a first lumen 130 having a size and shape commensurate with an exterior size and shape of the housing 60. Further, and as best shown in FIG. 1, the catheter 52 forms an exit port 132 that is fluidly open to the first lumen 130. The exit port 132 is sized to permit passage or deployment of individual ones of the clips 34 and thus is aligned with the deployment window 90 of the housing 60 upon final assembly. The exit port 132 can have a size and shape corresponding with those of the deployment window 90; in other constructions, the exit port 132 can be larger than the deployment window 90.

Returning to FIG. 8, the catheter 52 can form additional lumens. For example, FIG. 8 reflects the catheter 52 forming optional second and third lumens 134, 136. The second lumen 134 is sized to slidably receive the guide wire 36 (FIG. 1). The third lumen 156 is configured for operable connection to the biasing device (not shown) as described below. For example, where the biasing device includes an inflatable balloon or similar structure, the third lumen 136 provides a conduit for delivery and evacuation of an inflation fluid (e.g., gas) in operating the biasing device.

Returning to FIG. 1, and as indicated above, the instrument 32 can optionally include the introducer 54 that is configured for attachment to at least one of the delivery assembly 50 and the catheter 52. The introducer 54 can be assembled over a portion of the housing 60 or can be entirely distal the catheter 38. Regardless, the introducer 54, where provided, forms or includes a distally tapering diameter tip or cone 140 that promotes atraumatic atrial delivery of the instrument 32. Further, with embodiments in which the stapling apparatus 30 includes the guide wire 36, the introducer 54 can form a longitudinal passageway 142 sized to slidably receive the guide wire 36 with over-the-wire delivery techniques.

Figure 9:
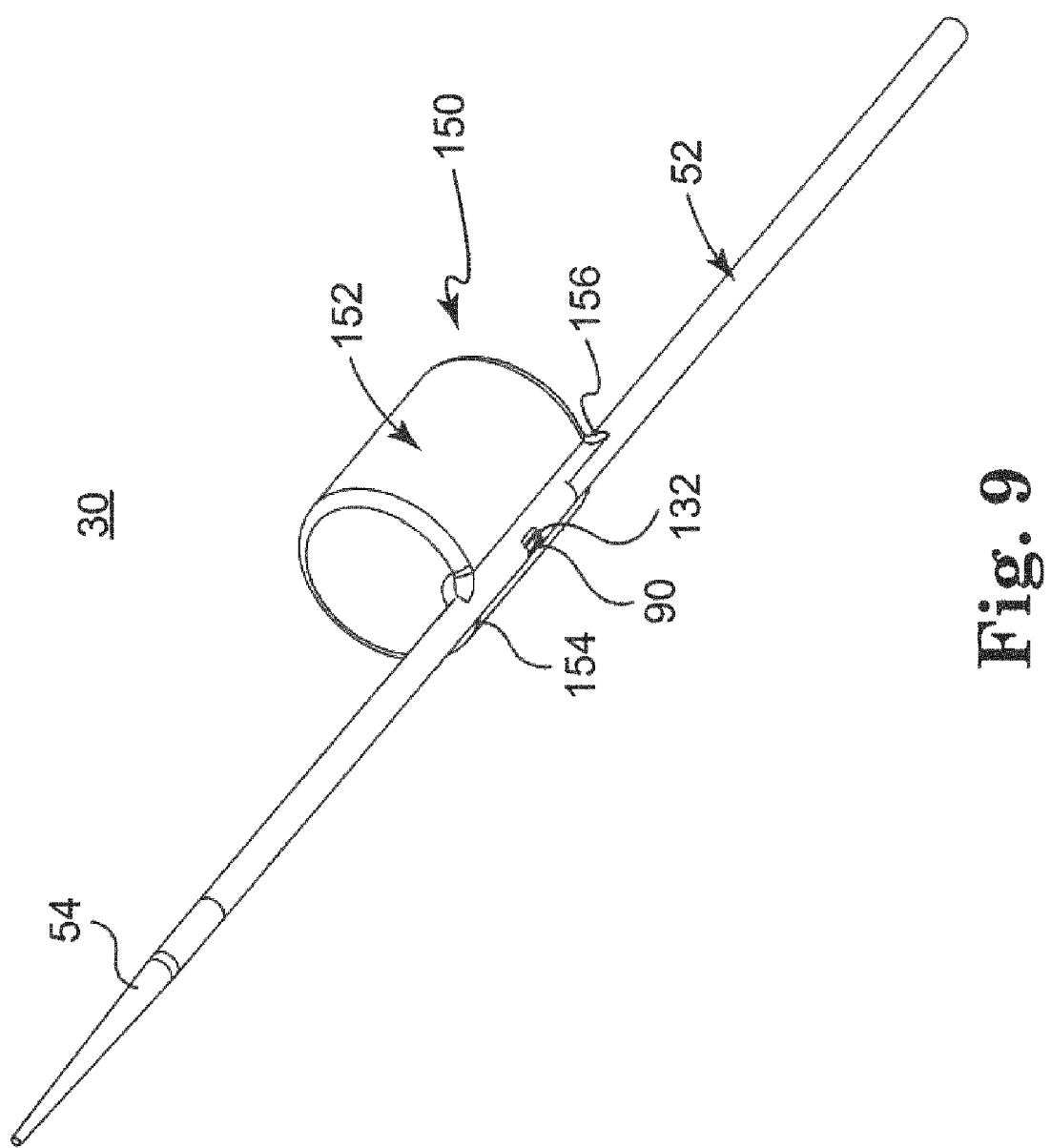
FIG. 9 is a perspective view of the apparatus of FIG. 1, illustrating a biasing device in accordance with principles of the present disclosure.

The stapling device 32 can further optionally include a biasing or expansion device. Construction of components of one possible biasing device 150 useful with the stapling apparatus 30 is shown in FIG. 9. In general terms, the biasing device 150 includes a balloon 152 or similar expandable structure attached (e.g., sealed) at opposing ends 154, 156 thereof to the catheter 52. The balloon 152 is inflatable to the expanded state of FIG. 9, and is arranged such that a maximum point of expansion relative to the catheter 52 is opposite the exit port 132/deployment window 90. That is to say, while the lumen through which inflation medium is delivered to and from an interior of the balloon 152 (e.g., the third lumen 136 of FIG. 8) may not necessarily be directly opposite the exit port 132/deployment window 90, the balloon 152 is arranged on the catheter 52 such that when inflated, the balloon 152 will force the exit port 132 side or surface of the catheter 52 into contact with a desired anatomical structure, and the balloon 152 will not interfere with this desired placement. Though not shown in the figures, with the biasing device 150 construction of FIG. 9, the catheter 52 forms an inflation port that establishes fluid communication between the third lumen 136 and an interior of the balloon 152.

The biasing device 150 can assume a variety of forms differing from that shown in FIG. 9. For example, the balloon 152 can be disposed within the catheter 52 in a retracted (e.g., deflated) state. Alternatively, the balloon 152 can be replaced by a mechanical-type biasing device, such as a mesh or braided structure formed as an expandable/retractable cage. In yet other embodiments, the biasing device 150 can be eliminated. Regardless, FIG. 9 illustrates the stapling apparatus 30 upon final assembly, with the delivery assembly 50 (FIG. 1) and corresponding clips 34 (FIG. 1) disposed within the catheter 52, and the introducer 54 forming a distal-most component of the stapling apparatus 30.

Figure 10:
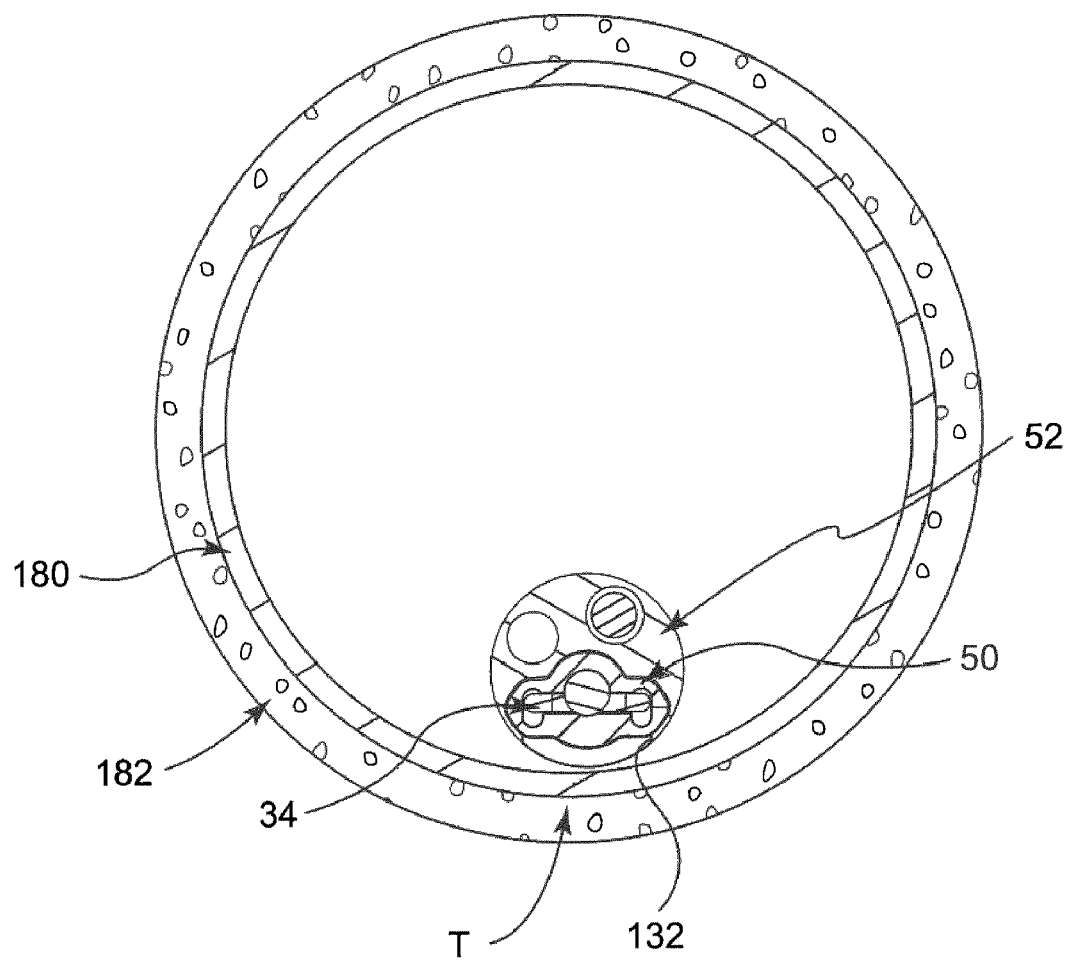
FIG. 10 is a simplified illustration of a portion of the apparatus of FIG. 1 relative to a vascular target site prior to deployment of the clips.

During use, the stapling apparatus 30 can be employed in securing an endovascular graft 180 to a vessel wall 182 of a body lumen as generally shown in FIG. 10, for example. In general terms, the instrument 32 is manipulated to deliver the loaded delivery assembly 50/catheter 52 to the position of FIG. 10 via the vascular tree of the patient until the delivery assembly 50 reaches a target site T. For example, the instrument 32 can be delivered over the guide wire 36 following threading of the guide wire 36 to the target site T. The exit port 132 of the catheter 52 (and thus the deployment window 90 (not shown) of the delivery assembly 50) is located against the target site T at which placement of one of the clips 34 is desired. In this regard, the optional biasing device (e.g., the biasing device 150 of FIG. 9), can be actuated to force or bias the exit port 132 against the target site T. Regardless, once the treating clinician perceives the exit port 132 to be appropriately positioned, one of the clips 34 can then be deployed.

Figure 11A:
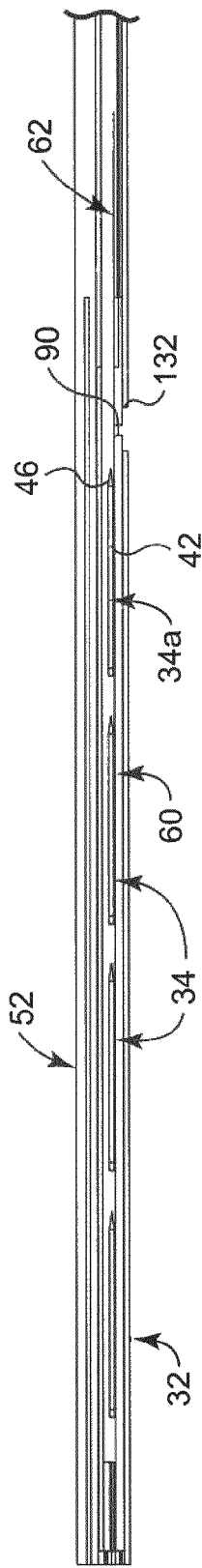
FIGS. 11A-11C illustrate operation of the apparatus of FIG. 1 in deploying a clip.
Figure 11B:
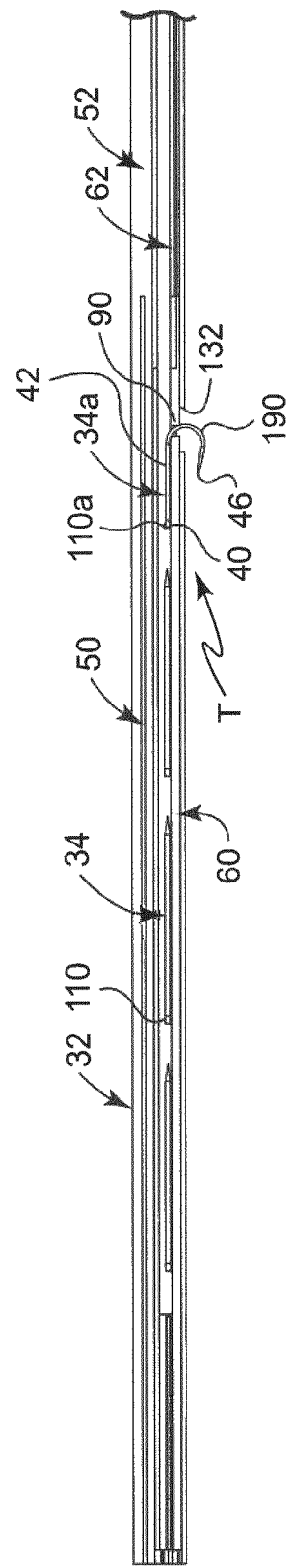
Figure 11C:
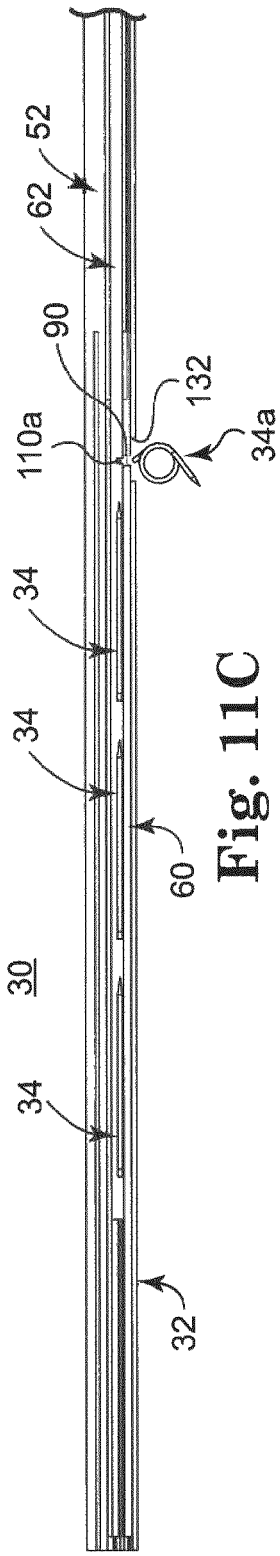

In particular, and with reference to FIGS. 11A-11C (that otherwise illustrate a distal portion of the instrument 32 with the introducer 54 (FIG. 1), the biasing device 150 (FIG. 9), and the guide wire 36 (FIG. 1) removed), as initially provided, each of the clips 34 are distal the deployment window 90 (and thus the distal exit port 132). Deployment of a first one of the clips 34a from the position of FIG. 11A begins with the clinician proximally retracting the deployment rod 62 relative to the housing 60 (rightward relative to the orientations of FIGS. 11A-11C). The first clip 34*a* (as well as others of the clips 34 in some embodiments) moves proximally relative to the housing 60 with the proximal retraction of the deployment rod 62, bringing the legs 42, 44 of the first clip 34*a* (it being understood that only the first leg 42 is visible in the view of FIGS. 11A-11C) proximally toward the deployment window 90.

With continued proximal retraction of the deployment rod 62, the respective ends 46, 48 of the legs 42, 44 of the first clip 34*a* are radially aligned with the deployment window 90 and thus the exit port 132. With further proximal movement of the deployment rod 62, a portion of the legs 42, 44 is exposed or removed from the confines of the housing 60. More particularly, and as reflected in the partial deployment state of FIG. 11B, the shape memory characteristic of the clip 34*a* causes an exposed or deployed portion 190 of the legs 52, 54 to self-revert toward the natural loop-shape described above, thereby passing through the deployment window 90 and the exit port 132. Notably, the bridge 40 remains captured within the delivery assembly 50, and in particular between the housing 60 and the corresponding notch 110*a* of the deployment rod 62. Thus, the clip 34*a* will not completely self-deploy from the position of FIG. 11B. Instead, further proximal movement of the deployment rod 62 is required.

The above-described captured relationship of the first clip 34*a* relative to the housing 60/deployment rod 62 affords the clinician the ability to evaluate a position of the clip 34*a* in the partially-deployed state relative to the target site T. That is to say, in the partially-deployed state of FIG. 11B, an approximate location of the clip 34*a* relative to the target site T (referenced generally in FIG. 11B) upon subsequent, complete deployment of the clip 34*a* can be directly, visually perceived by the clinician by gauging a spatial position of the deployed portion 190 relative to the target site T. Under circumstances where the clinician deems the indicated clip location to be unsatisfactory (or under other circumstances), the exposed portion 190 of the clip legs 42, 44 can be retracted or withdrawn back into the delivery assembly 50 (and in particular the housing 60) by distally sliding or moving the deployment rod 62 relative to the housing 60. In this regard, because the corresponding notch 110*a* of the deployment rod 62 provides engagement surfaces or walls (e.g., the walls 112, 114 (FIG. 6B)) at both sides of the bridge 40, distal movement of the deployment rod 62 is imparted onto the bridge 40, thereby causing the first clip 34*a* (as well as all other clips 34 engaged by the deployment rod 62 via the corresponding notches 110) to move distally, thereby pulling or forcing the exposed leg portion 190 back into the housing 60 (e.g., returning to the initial state of FIG. 11A). The clinician can then maneuver the instrument 32 relative to the target site T as desired, bringing the exit port 132 (and thus the deployment window 90) to a different position relative to the target site T as desired. Once so-positioned, the above steps can be repeated, including proximally retracting the deployment rod 62 to at least partially deploy the clip 34*a* via the deployment window 90/exit port 132, withdrawing of the clip 34*a* back into the housing 60, and repositioning the instrument 32.

Once the clinician has confirmed desired location of the exit port 132/deployment window 90, proximal retraction of the deployment rod 62 relative to the housing 60 is continued until the corresponding notch 110*a* is approximately aligned with the deployment window 90. As shown in FIG. 11C, then, the bridge 50 is no longer captured between the housing 60 and the deployment rod 62, thereby allowing the clip 34*a* to fully release or deploy from the instrument 32 and into the target site T. The remaining clips 34 can be deployed in a similar manner, with the stapling apparatus 30 providing the clinician with an ability to repeatedly, partially-deploy one or more the remaining clips 34 along with re-positioning of the instrument 32 as desired.

Figure 12:
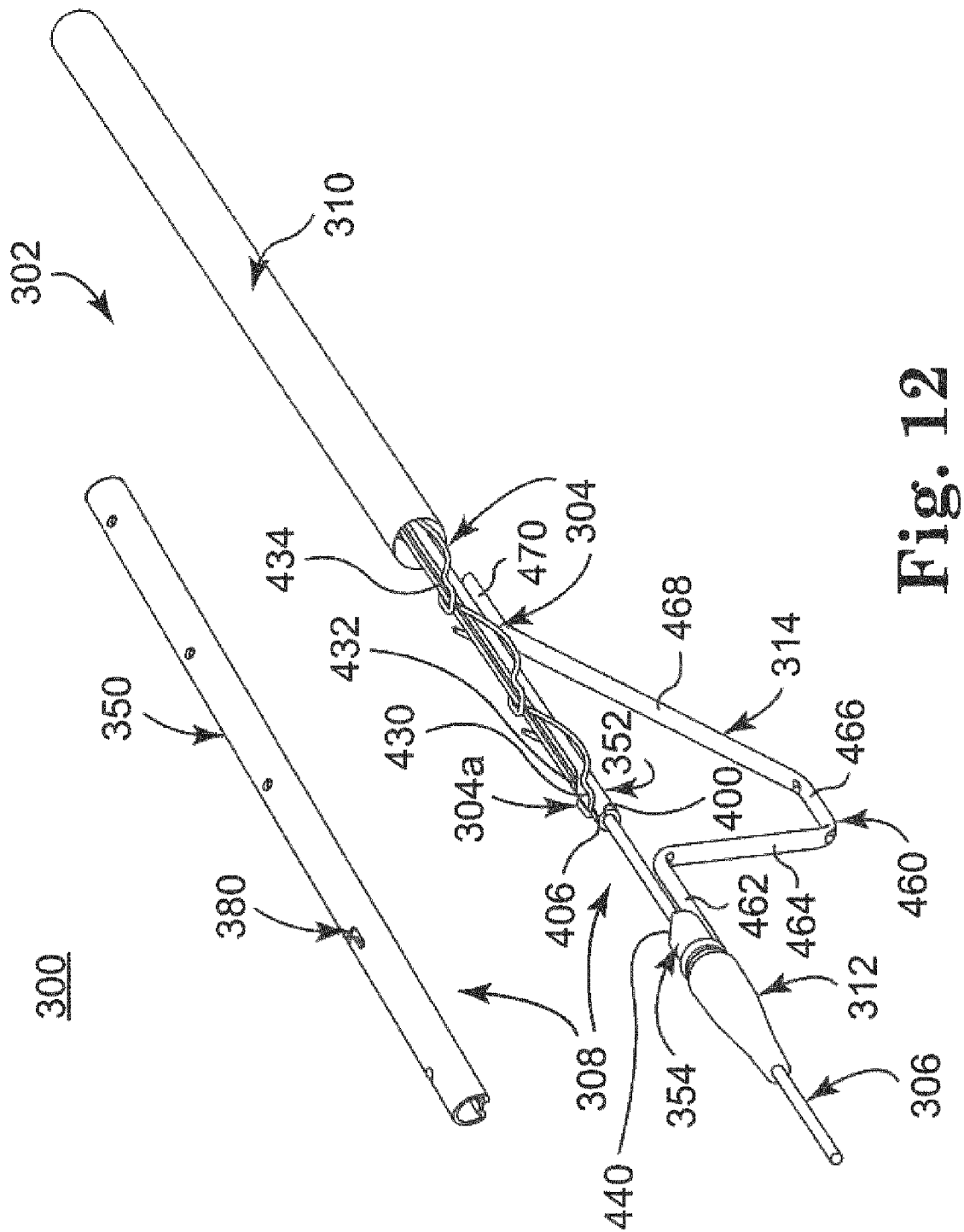
FIG. 12 is a perspective, partially exploded view of another endovascular stapling apparatus in accordance with principles of the present disclosure.

Portions of another embodiment endovascular stapling apparatus 300 in accordance with aspects of the present disclosure are shown in FIG. 12. The apparatus 300 includes a delivery instrument 302 (referenced generally) maintaining a plurality of self-closing clips 304. The apparatus 300 can further include a guide wire 306, with the instrument 302 including a delivery assembly 308, a catheter 310, an actuator or handle (not shown), an optional introducer 312, and an optional biasing or expansion device 314. Details on the various components are provided below. In general terms, however, the instrument 302 maintains the clips 304 in a biased state (reflected in FIG. 12), and is operable via the actuator to selectively deploy ones of the clips 304 from the delivery assembly 308. Where provided, the guide wire 306 and the introducer 312 facilitate desired placement of the delivery assembly 308 to a target site. Similarly, the optional biasing device 314 operates to offset or counter forces generated by use of the delivery assembly 308, as well as facilitating delivery of the clips 304 at desired locations relative to a vessel wall and/or graft. Regardless, the instrument 302 provides the treating clinician with the ability to partially deploy and retract the clips 34 during use.

Figure 13A:
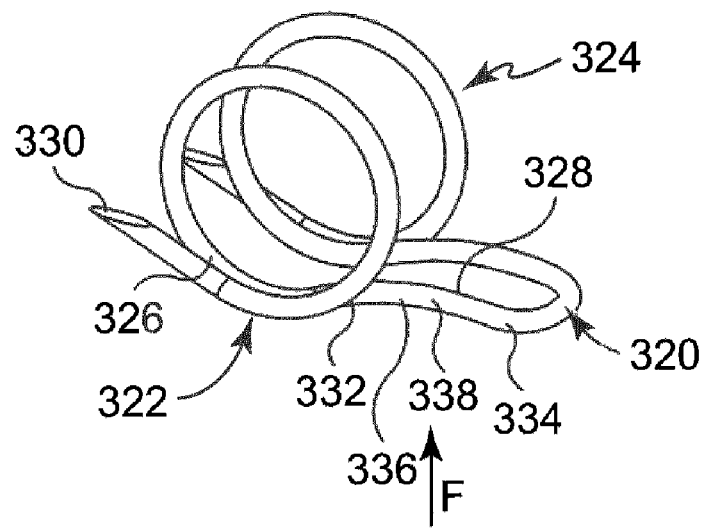
FIGS. 13A and 13B are enlarged, perspective views of a clip useful with the apparatus of FIG. 12.
Figure 13B:
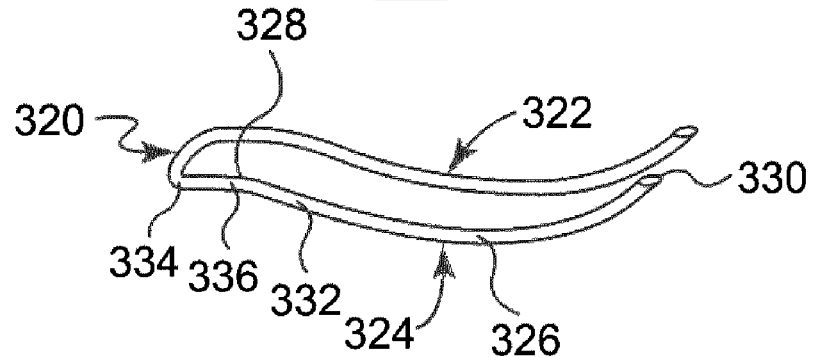

As with the stapling apparatus 30 (FIG. 1) described above, certain features of the delivery assembly 308 are better understood relative to components of the clips 304. With this in mind, FIG. 13A illustrates one of the clips 304 in accordance with some embodiments in greater detail. Once again, the clip 304 is transitionable from the natural or undeformed state of FIG. 13A to the biased state reflected in FIG. 13B, and self-reverts back from the biased state to the natural or undeformed state. Thus, in some embodiments, the clip 304 incorporates a shape memory attribute as described above. As a point of reference, the biased state of FIG. 13B is accomplished when the clip 304 is subjected to external constraining forces (not shown), and can include the clip 304 assuming a variety of other shapes differing from that of FIG. 13B. The shape of FIG. 13B reflects a configuration of the clip 304 when constrained within the delivery assembly 308 in accordance with but one contemplated embodiment.

The clip 304 includes a bridge 320 interconnecting opposing legs 322, 324. Each of the legs 322, 324 includes or defines a staple region 326 and a neck region 328. The staple region 326 extends from the neck region 328 and, in the natural undeformed state of FIG. 13A, forms a loop-like shape that can be an overlapping loop as illustrated or can be non-overlapping. As a point of reference, in the biased state of FIG. 13B, the staple region 326 is forced to a relatively straight shape as compared to the natural state. Further, the staple region 326 terminates at an end 330 that can be sharpened to promote piercing of target tissue, or can be blunt.

The neck region 328 extends between the staple region 326 and the bridge 320, and forms or defines a curved or curvilinear shape in longitudinal extension. More particularly, the neck region 328 can be defined as having a first side 332 at the transition from the staple region 326, a second side 334 at a transition to the bridge 320, and an intermediate segment 336 between the sides 332, 334. With these designations in mind, the intermediate segment 336 extends or curves generally upwardly (relative to the orientation of FIG. 13A) from the first side 322 to a center point 338, and generally downwardly from the center point 338 to the second side 334. In other words, the center point 338 is laterally offset from the sides 332, 334. With this configuration, then, the neck region 328 naturally biases the bridge 320 in a generally downward direction (relative to the orientation of FIG. 13A). Stated otherwise, the neck region 328 resists a force F applied to the bridge 320, especially in instances where the center point 338 is externally supported.

Returning to FIG. 12, and with the above parameters of the clips 304 in mind, the delivery assembly 308 includes, in some embodiments, a housing 350, a deployment rod 352, and a stop member 354. In general terms, the deployment rod 352 is slidably disposed within the housing 350, and is adapted to interface with the clips 304 as described below. Further, the housing 350 is adapted to retain the clips 304 in a biased state (e.g., the shape of FIG. 13B) and permit deployment of the clips 304 therefrom. Finally, the stop member 354 facilitates desired positioning of the deployment rod 352 in effectuating deployment of the clips 304 from the housing 350.

As shown in FIG. 14A, the housing 350 is an elongated, tubular body defining an internal channel 360 extending between, and open relative to, proximal and distal ends 362, 364. With further reference to FIG. 14B, the channel 360 includes or is defined by, in some embodiments, a central segment 366 and opposing side segments 368, 370. The segments 366-370 are open relative to one another, and are sized in accordance with the deployment rod 352 (FIG. 12) and the clips 304 (FIG. 12). For example, the central segment 366 is generally circular in transverse cross-section, defining a shape or diameter commensurate with (e.g., slightly greater than) a corresponding shape of the deployment rod 352. The side segments 368, 370 are generally identical in shape, and are configured to slidably maintain the legs 322, 324 (FIG. 13A) of the clips 304 in a manner that forces or constrains the legs 322, 324 to a desired shape. In some embodiments, then, the side segments 368, 370 are sized and positioned (relative to the central segment 366) for receiving a portion of the legs 322, 324 of each of the clips 304, constraining or biasing the legs 322, 324 to the shape of FIG. 13B.

A length of the housing 350 is selected to accommodate a desired number of the clips 304 (in the deformed, relatively straight state) arranged end-to-end (i.e., the longitudinal arrangement of the clips 304 as shown in FIG. 12). In some embodiments, then, the housing 350 is sized to retain four of the clips 304, although in other embodiments, any other number of clips 304 can be housed. Regardless, the housing 350 forms a deployment window 380 through a side wall thereof, and open to the internal channel 360. The deployment window 380 is generally sized and shaped to permit release or deployment of the one of the clips 304 from the channel 360. For example, FIG. 14C illustrates one embodiment of the deployment window 380 in greater detail, including or defining a central portion 382 and opposing side portions 384, 386. The central portion 382 is sized and shaped in accordance with the bridge 320 (FIG. 13A) of the clip 304, whereas the side portions 384, 386 are sized to permit passage of a respective one of the legs 322 or 324 (FIG. 13A). The central portion 382 interconnects (i.e., is open to) the side portions 384, 386 intermediately along a length thereof. For example, the central portion 382 divides each of the side portions 384, 386 into a proximal region 388 and a distal region 390, with the distal region 390 being longer than the proximal region 388. Alternatively, the deployment window 380 can have other shapes and/or sizes.

The deployment rod 352 is shown in greater detail in FIG. 15, and comprises an elongated body defining a distal end 400 and a proximal end 402. In some embodiments, the deployment rod 352 is a tubular body, forming a lumen 404 extending between, and open relative to, the distal and proximal ends 400, 402. Where provided, the lumen 404 can be sized to slidably receive the optional guide wire 306 (FIG. 12). Alternatively, the deployment rod 352 can be a more solid body. Regardless, the deployment rod 352 forms various features for interfacing with the clips 304 (FIG. 12), including a capture notch 406 and a shuttle surface 408.

The notch 406 is formed adjacent the distal end 400. In this regard, a location of the notch 406 relative to the distal end 400 is selected as a function of the clips 304 (FIG. 12) as constrained within the housing 350 (FIG. 14A), and of corresponding features of the housing 350 as described below. In more general terms, the notch 406 is formed or defined by a distal side wall or surface 410 and a proximal side wall or surface 412 that combine to define a width of the notch 406. The notch width is commensurate with a diameter (or other outer major dimension) of the bridge 320 (FIG. 13A) of the clips 304, such that the bridge 320 can be received or partially captured within the notch 406. In this regard, each of the walls 410, 412 is configured to impart or transfer a sliding force from the deployment rod 352 onto the so-received clip 304. For example, and with additional reference to FIG. 12, a retraction or pulling force applied to the deployment rod 352 (in the proximal direction) is imparted onto the clip 304a otherwise received within the notch 406; similarly, distal movement of the deployment rod 352 is transferred onto the clip 304a via the proximal wall 412. Notably, however, in the absence of an external constraining force (i.e., the housing 350), a relationship between the size of the notch 406 and of the bridge 320 is such that the clip 304a is freely releasable from the notch 406.

The shuttle surface 408 extends proximal the notch 406, and includes a leading region 430, a ramp 432, and a trailing region 434. In general terms, the shuttle surface 408 serves to direct the clips 304 (FIG. 12) from the trailing region 434 to the notch 406 via a sliding interface. In this regard, a radial elevation of the shuttle surface 408 is closer to a center axis C of the deployment rod 352 along the trailing region 434 as compared to a spatial position along the leading region 430, with the ramp 432 serving as a transition from the trailing region 434 to the leading region 430. This radial increase in a spatial location or elevation of the shuttle surface 408 relative to the center axis C is reflected in FIGS. 16A-16C. FIG. 16A illustrates the shuttle surface 408 along the leading segment 420. The shuttle surface 408 is comparatively closer to the center axis C along the ramp 432 as reflected in FIG. 16B, with the even closer spatial location along the trailing region 434 being shown in FIG. 16C.

Figure 17C:
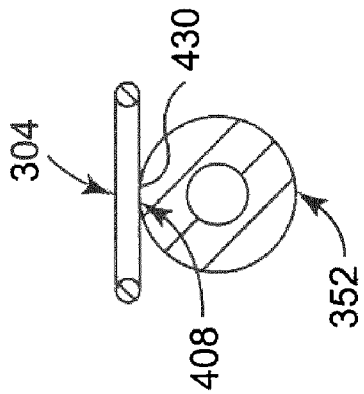
FIGS. 17A-17C are cross-sectional views of the deployment rod of FIG. 15 along with a clip.
Figure 17B:
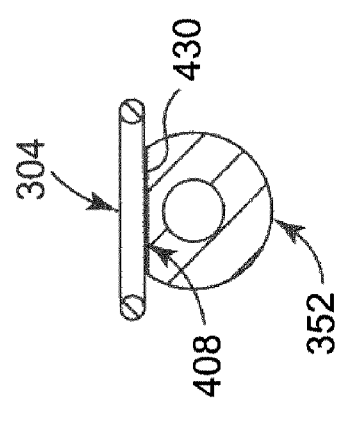
Figure 17A:
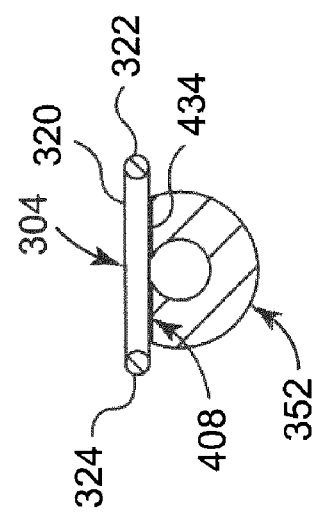

Returning to FIG. 15, the shuttle surface 408 is relatively smooth, free of any abrupt protrusions or apertures that might otherwise impede sliding movement of the clips 304 (FIG. 12) thereon. That is to say, unlike the notch 406, the shuttle surface 408 is not configured to partially capture or retain the clips 304; instead, the clips 304 freely slide along the shuttle surface 408, and vice-versa. For example, FIG. 17A illustrates one of the clips 304 relative to the shuttle surface 408 along the trailing region 434. The bridge 320 is disposed along the shuttle surface 408 (it being understood that the housing 350 (FIG. 14A) serves to constrain the clip 304 in a sliding relationship relative to the shuttle surface 408). As illustrated, the deployment rod 352 has an outer diameter that is less than a lateral spacing between the legs 322, 324, and thus does not impede movement of the deployment rod 352 and the clip 304 relative to one another. Sliding interface between the bridge 320 and the shuttle surface 408 is similarly maintained at the ramp 432 (FIG. 17B) and the leading region 430 (FIG. 17C). As described below, an inherently inward bias of the clip 304 causes the bridge 320 to transition into the notch 406 (FIG. 14A) when positioned distally beyond the leading region 430 of the shuttle surface 408.

Returning to FIG. 12, a longitudinal length of the leading region 430 is selected as a function of a size of the clips 304 (as constrained by the housing 350), as well as other features of the housing 350. In general terms, a longitudinal length of the leading region 430 (and thus a longitudinal location of the ramp 432) is sized such that only a single one of the clips 304 is interfaced therealong at a single time. Conversely, a longitudinal length of the trailing region 434 is sized in accordance with the number of the clips 304 initially loaded into the delivery assembly 308. Thus, for example, the trailing region 434 is sized to simultaneously maintain at least three of the clips 304 as described below.

Figure 18:
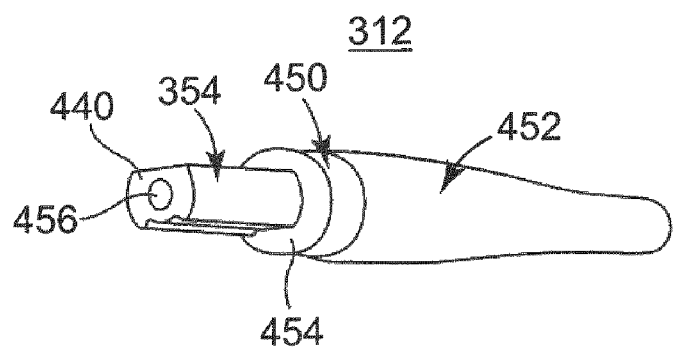
FIG. 18 is an enlarged, perspective view of an introducer portion of the apparatus of FIG. 12.

The stop member 354 is sized for placement within the channel 360 of the housing 350, and defines an engagement face 440 (referenced generally). In some embodiments, the stop member 354 is provided as an integral part of the introducer 312. For example, as shown in FIG. 18, the introducer 312 can include the stop member 354, a hub 450, and an introducer body 452. The hub 450 is sized for assembly to the housing 350 (FIG. 12), with the stop member 354 extending proximally therefrom. An axial length of the stop member 354, and in particular a longitudinal position of the engagement face 440 relative to an attachment end 454 of the hub 450, is selected in accordance with dimensional characteristics of the delivery assembly 308 (FIG. 12) as described below whereby the engagement face 440 is spatially positioned to interface with the deployment rod 352 (FIG. 12) at a predetermined location. Regardless, the introducer body 452 extends distally from the hub 450 and has a tapered shape conducive for atraumatic atrial insertion techniques. Finally, an axial passage 456 extends through the stop member 354 and the introducer body 452, and is sized to slidably receive the optional guide wire 308 (FIG. 12). While the stop member 354 has been described as being an integrally formed component of the introducer 312, in other embodiments the stop member 354 can be a separately-formed component. In yet other embodiments, the stop member 354 can be an integrally-formed feature of the housing 350.

Returning to FIG. 12, the optional biasing or expansion device 312 can take any of the forms previously described (e.g., an expandable balloon or braided mesh). Alternatively, and with the construction of FIG. 12, the biasing device 312 includes a linkage assembly 460, having first-fifth links 462-470. The links 462-470 can be movably connected to one another in a variety of fashions, such as via corresponding living hinges as shown; alternatively, one or more mechanical hinge components (e.g., pins) can be employed. Regardless, and with additional reference to FIG. 19, the linkage assembly 460 is assembled to the housing 350 so as to radially extend (and retract) at least the third link 466 relative to the housing 350 (and in particular, in a direction opposite of the deployment window 380) via sliding movement of the fifth link 470 relative to the first link 462.

Figure 19:
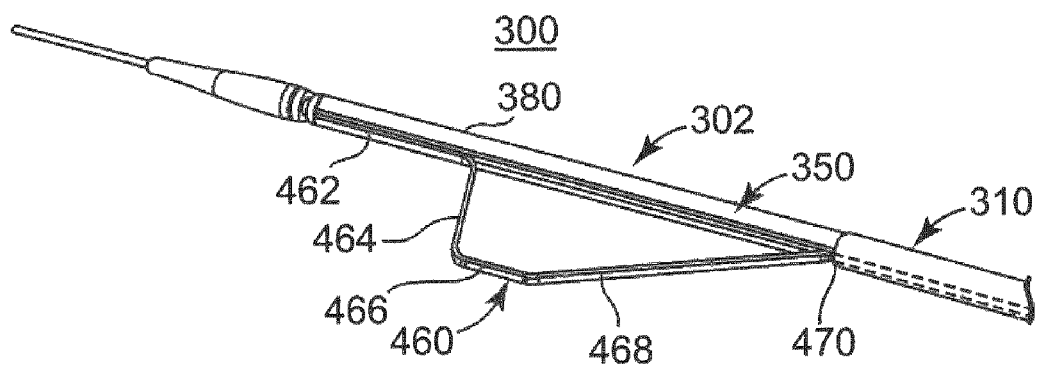
FIG. 19 is a perspective view of the apparatus of FIG. 12, illustrating a biasing device in accordance with principles of the present disclosure.

Desired, selective articulation of the linkage assembly 460 can be achieved by rigidly affixing (e.g., adhesive bond) the first link 462 to the housing 350 along a side thereof opposite the deployment window 380 (referenced generally). The remaining links 464-470 extend proximally from the first link 462 as shown, with the fifth link 470 being slidably maintained along the housing 350. For example, the instrument 302 can further include the sheath or catheter 310 within which the housing 350 and the linkage assembly 460 are at least partially contained proximal the deployment window 380. With this construction, the fifth link 470 (or an additional body connected to the fifth link 470) slidably extends proximal the catheter 310 for manipulation thereof by the treating clinician. More particularly, distal movement of the fifth link 470 causes the second end and fourth links 464, 468 to deflect relative to the first and fifth links 462, 470, respectively (via corresponding hinged relationships), thereby positioning the third link 466 radially away from the housing 350 as shown in FIG. 19. Conversely, with proximal retraction of the fifth link 470 from the position of FIG. 19, the second-fourth links 464-468 are drawn toward, and into contact with, the housing 350.

Figure 20A:
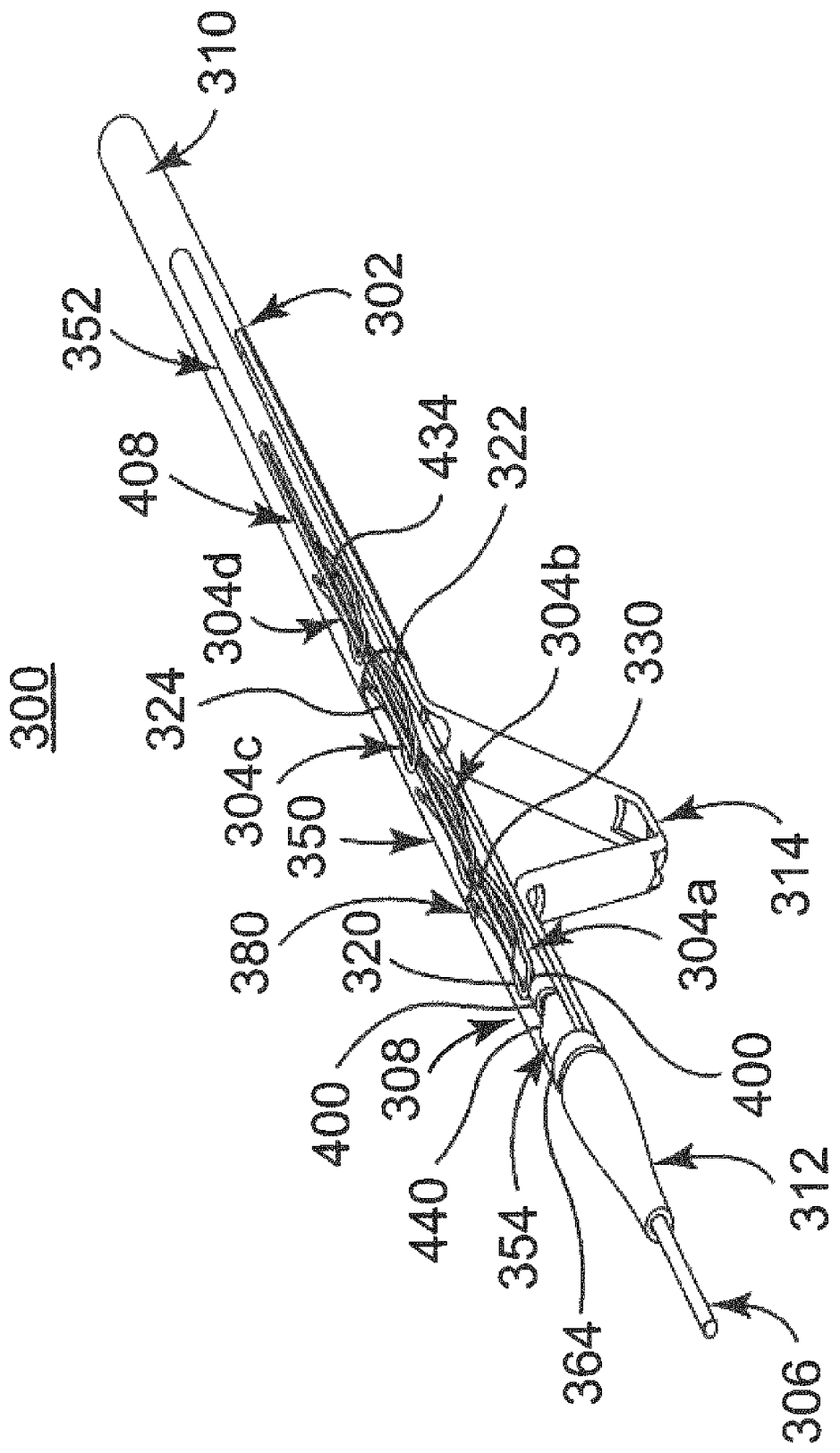
FIG. 20A illustrates the apparatus of FIG. 12 upon final assembly.

Construction of the stapling apparatus 300 to the initial, loaded state is shown in FIG. 20A and includes assembling the clips 304 within the deployment assembly 308. For ease of illustration, the housing 350 is shown in phantom in FIG. 20A. The deployment rod 352 and the clips 304 are co-axially disposed within the channel 360 (FIG. 14A) of the housing 350. For example, with respect to the loaded state of FIG. 20A, four of the clips 304 are provided, including the first clip 304a and second-fourth clips 304b-304d. The clips 304a-304d are arranged end-to-end, with the bridge 320 of the first clip 304a being positioned within the notch 406 of the deployment rod 352. The bridges 320 of the remaining clips 304b-304d are arranged over the trailing region 434 of the shuttle surface 408. Further construction of the instrument 302 includes the stop member 354 assembled to the housing 350, positioning the engagement face 440 proximal the distal end 364 and longitudinally spaced from the deployment window 380 by a predetermined distance for reasons made clear below.

Additional, optional components of the instrument 302 can further be assembled as desired. For example, the introducer 312 (where provided apart from the stop member 354) can be assembled to the housing 350. Further, a biasing device, for example, the biasing device 314, can be assembled or otherwise associated with the housing 350, with or without the catheter 310. Finally, with embodiments of the apparatus 300 including the guide wire 306, the guide wire 306 can be coaxially fed through the deployment rod 352 and the introducer 312 prior to use or following delivery of the guide wire 306 to a target site.

In the initial, loaded state of FIG. 20A, the distal end 400 of the deployment rod 352 is proximally spaced from the engagement face 440 of the stop member 354. With this in mind, a spatial location of the notch 406 relative to the deployment window 380 correlates with a longitudinal length of the clips 304 (e.g., the first clip 304a) in the biased state shown such that with the bridge 320 of the first clip 304a nested within the notch 406, the ends 330 associated with the first clip 304a are positioned proximal the deployment window 380. An entirety of the second-fourth clips 304b-304d are also proximal the deployment window 380.

Operation of the instrument 302 in deploying one or more of the clips 304 is described below with reference to FIGS. 20A-20G. To better illustrate internal components, the housing 350 is shown in phantom in FIGS. 20A-20D and FIGS. 20F-20H. To initiate deployment of the first clip 304a, the deployment rod 352 is moved or slid distally relative to the housing 350 by the treating clinician via the actuator or handle (not shown) otherwise connected to a proximal region of the deployment rod 352. The first clip 304a moves with the deployment rod 352 due to the captured interface between the bridge 320 and the notch 406. Notably, however, remaining ones of the clips 304b-304d remain relatively stationary within the housing 350 with sliding movement of the deployment rod 352, with the shuttle surface 408 along the trailing region 434 simply sliding along or relative to the corresponding bridges 320. That is to say, in the biased state of FIG. 20A, the legs 322, 324 associated with each of the second-fourth clips 304b-304d are effectively, temporarily lodged or nested against surfaces of the housing 350 otherwise forming the channel 360 (FIG. 14A). Thus, even if a slight frictional interface is formed between the bridges 320 of the remaining clips 304b-304d and the shuttle surface 408, the remaining clips 304b-304d do not move with movement of the deployment rod 352.

Distal movement of the deployment rod 352, and thus of the first clip 304a, continues until the distal end 400 contacts the engagement face 440 of the stop member 354. In this regard, a longitudinal spacing between the engagement face 440 and the deployment window 380 corresponds with a longitudinal position of the notch 406 relative to the distal end 400 and a length of the clip 304a in the biased state such that when the deployment rod 352 contacts the stop member 354, the ends 330 of the first clip 304a are located within or at the deployment window 380. This relationship is reflected in FIG. 20B. Notably, however, the first clip 304a remains captured relative to the delivery assembly 302 via connection between the bridge 320 and the notch 406.

Figure 20B:
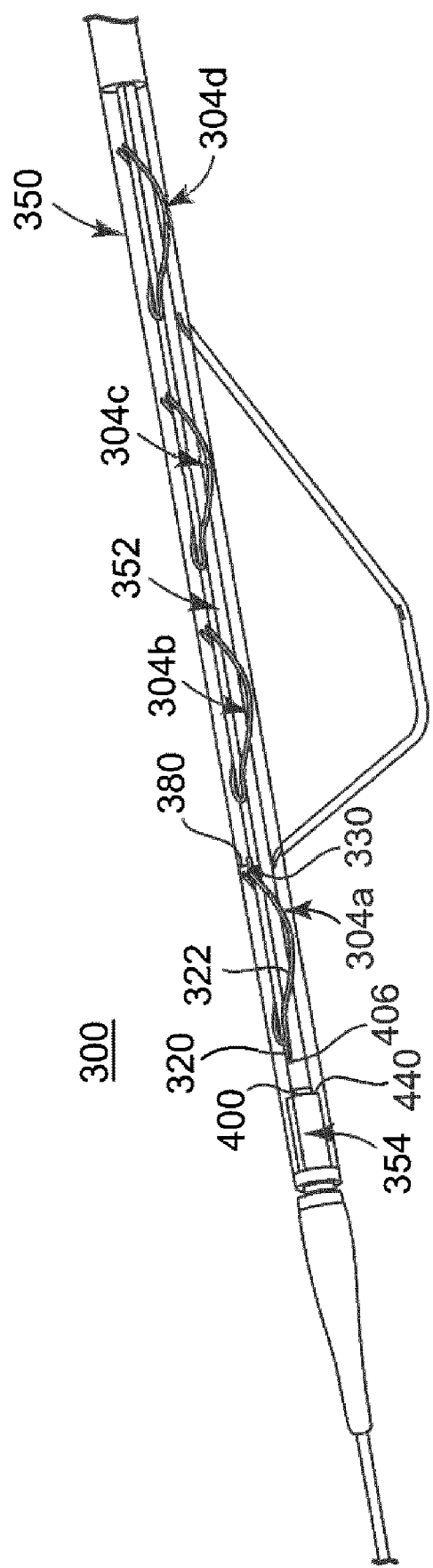
FIGS. 20B-20H illustrate operation of the apparatus of FIG. 12.
Figure 20C:
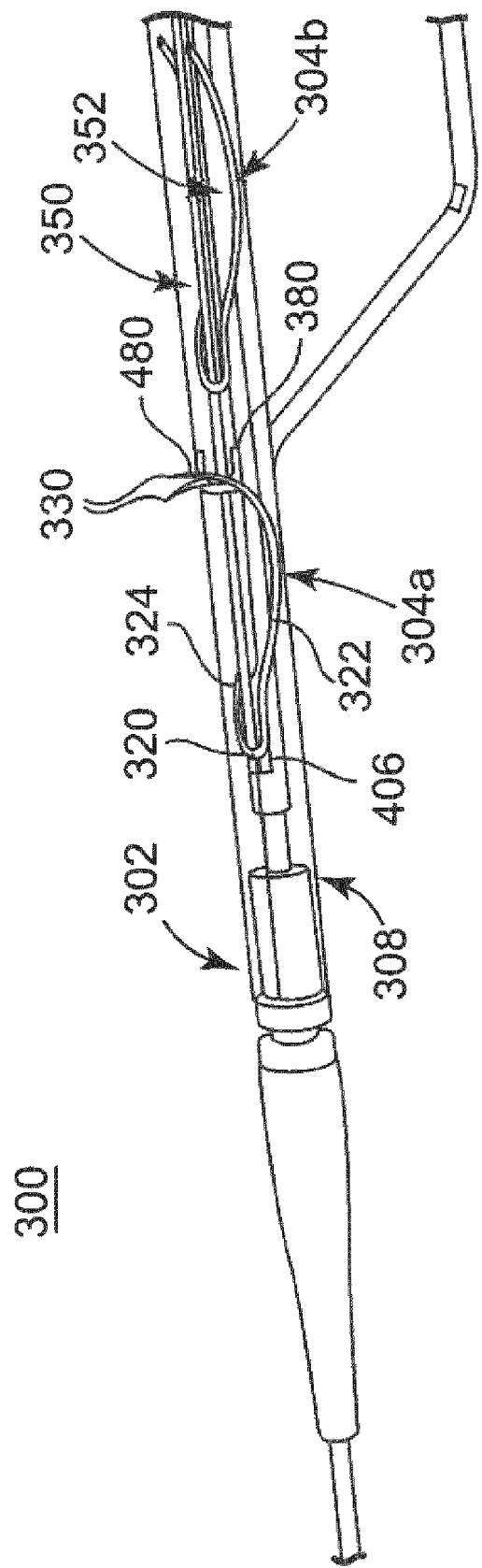
Figure 20D:
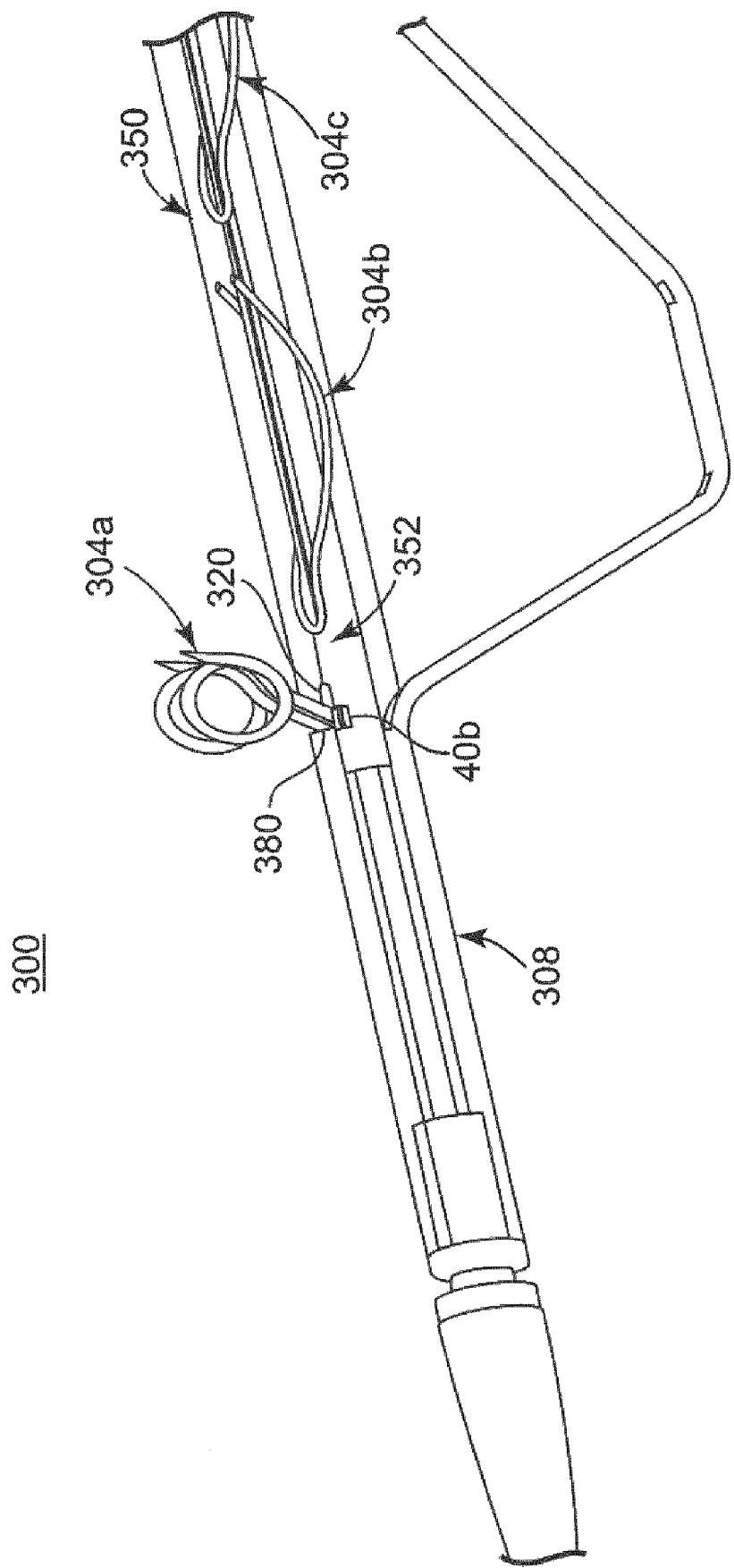
Figure 20E:
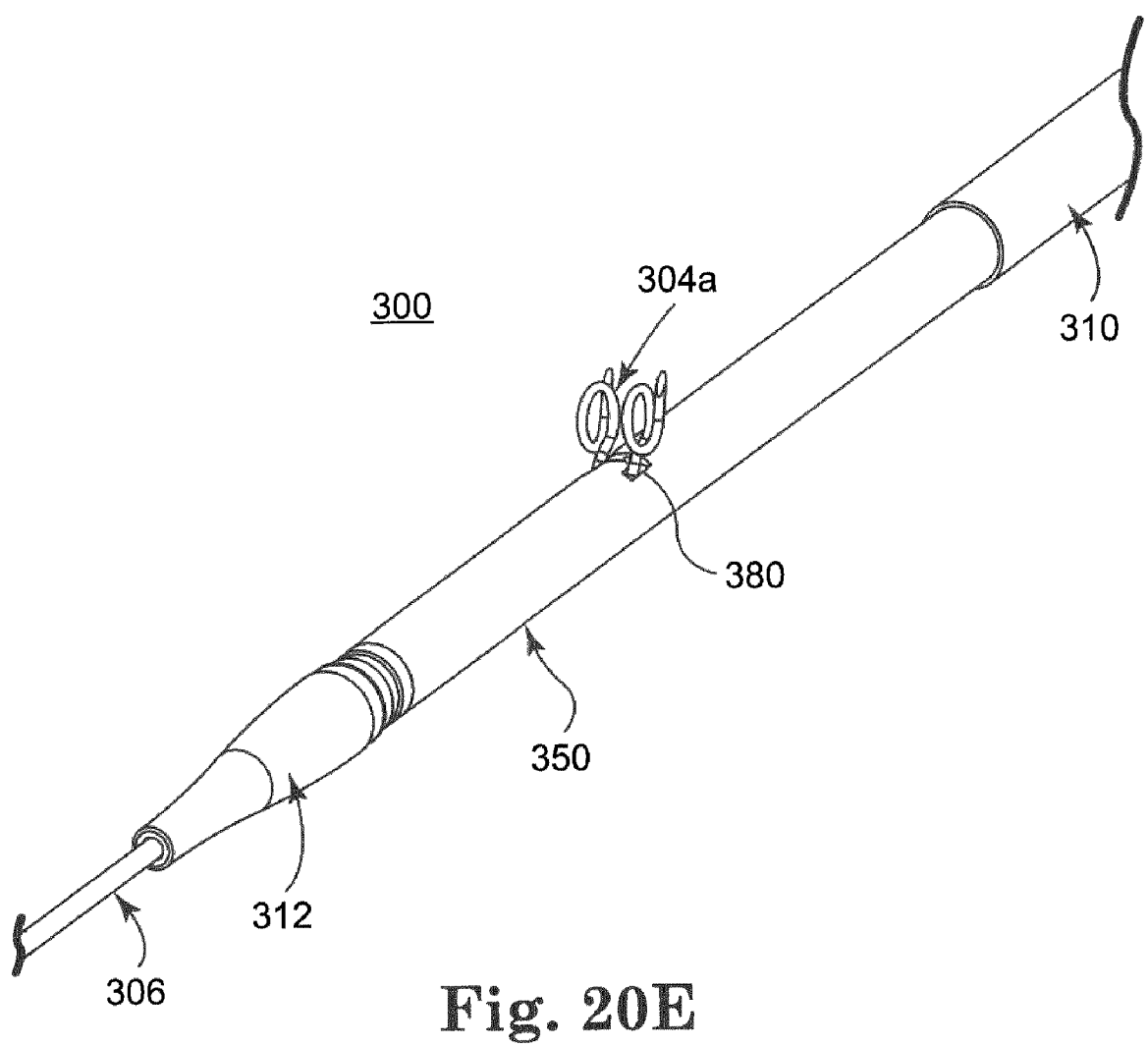

With subsequent proximal retraction of the deployment rod 352 relative to the housing 350 from the position of FIG. 20B, a portion of the legs 322, 324 is exposed or removed from the confines of the housing 350. More particularly, and as reflected in the partial deployment state of FIG. 20C, the shape memory characteristic of the clip 304a causes an exposed or deployed portion 480 of the legs 322, 324 to self-revert toward a natural loop-shape, thereby passing through the deployment window 380. Once again, with partial deployment of the clip 304a, the bridge 320 remains captured within the delivery assembly 308. Thus, the clip 304a will not completely self-deploy from the position of FIG. 20C. Instead, further proximal movement of the deployment rod 352 is required. Conversely, distal movement of the deployment rod 352 from the orientation of FIG. 20C withdraws or retracts the exposed portion 480 of the legs 322, 324 back into the housing 350 (e.g., back to the position of FIG. 20B). Thus, the instrument 302 affords the treating clinician the ability to selectively and repeatedly partially deploy and retract or withdraw the clip 304a.

Where complete deployment of the clip 304a is desired, proximal movement of the deployment rod 352 relative to the housing 350 continues from the position of FIG. 20C until the notch 406 is radially aligned with the deployment window 380. In this position, the bridge 320 is no longer captured between the housing 350 and the deployment rod 352, thereby allowing the clip 304a to fully release or deploy from the delivery assembly 308 as shown in FIGS. 20D and 20E.

Figure 20F:
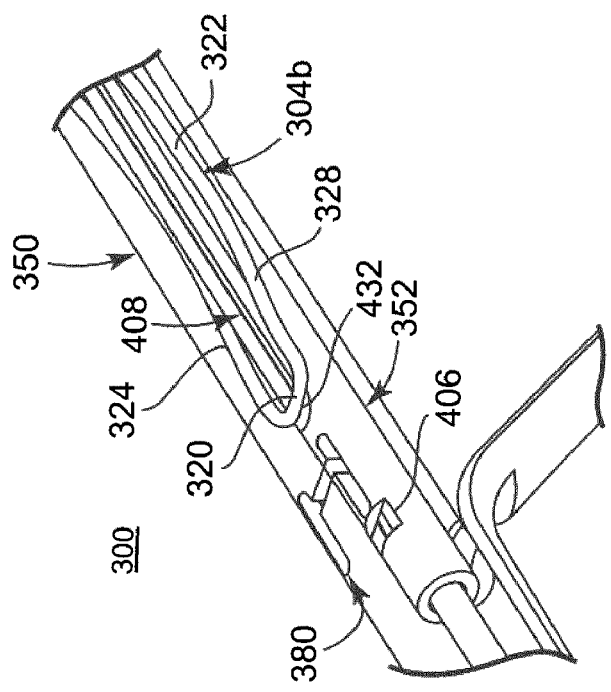
Figure 20G:
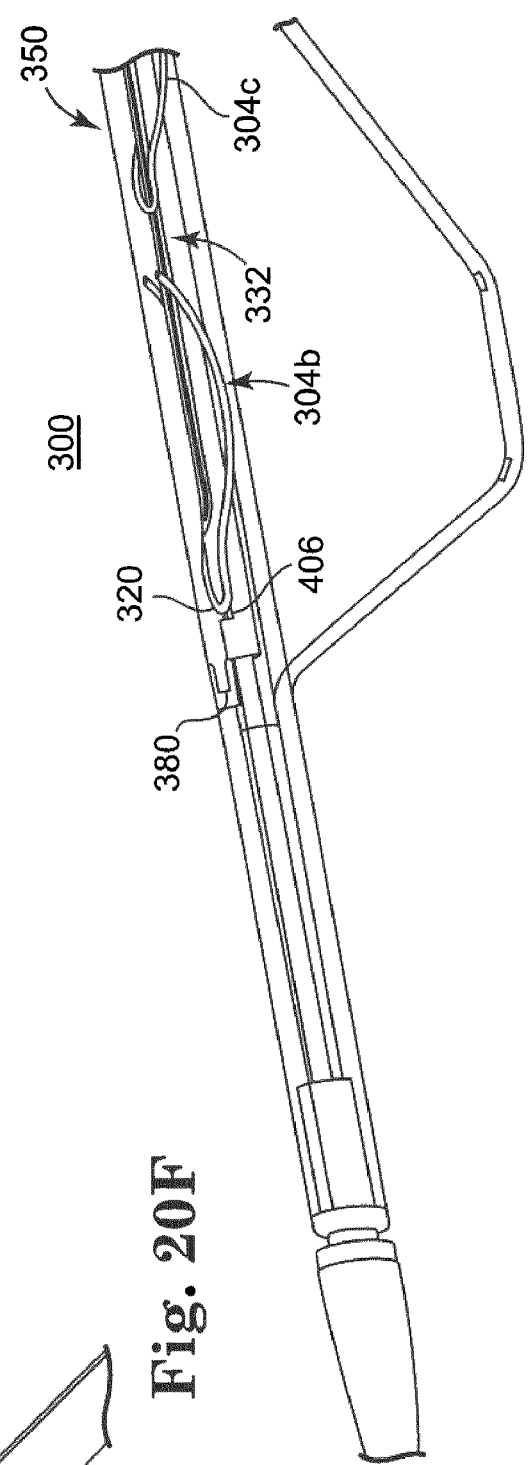

Throughout movements of the deployment rod 352 in deploying the first clip 304a, the remaining clips 304b-304d remain relatively stationary within the housing 350. Subsequent deployment of the second clip 304b entails proximally retracting the deployment rod 352 within the housing 350 from the position of FIG. 20D. In this regard, proximal movement continues, with the ramp 432 of the shuttle surface 408 brought into contact with the bridge 320 of the second clip 304b. As shown in FIG. 20F, then, interface between the bridge 320 and the ramp 432 causes, with further proximal movement of the deployment rod 352, the bridge 320 to move radially outwardly along the shuttle surface 408. With further proximal movement of the deployment rod 352, the bridge 320 is transitioned to the leading region 430 of the shuttle surface 408. Finally, as the notch 406 is brought into radial alignment with the bridge 320, the natural bias associated with the neck region 328 of each of the legs 322, 324 forces the bridge 320 to self-engage within the notch 406. FIG. 20G illustrates the bridge 320 of the second clip 304b self-transitioned into the notch 406.

Figure 20H:
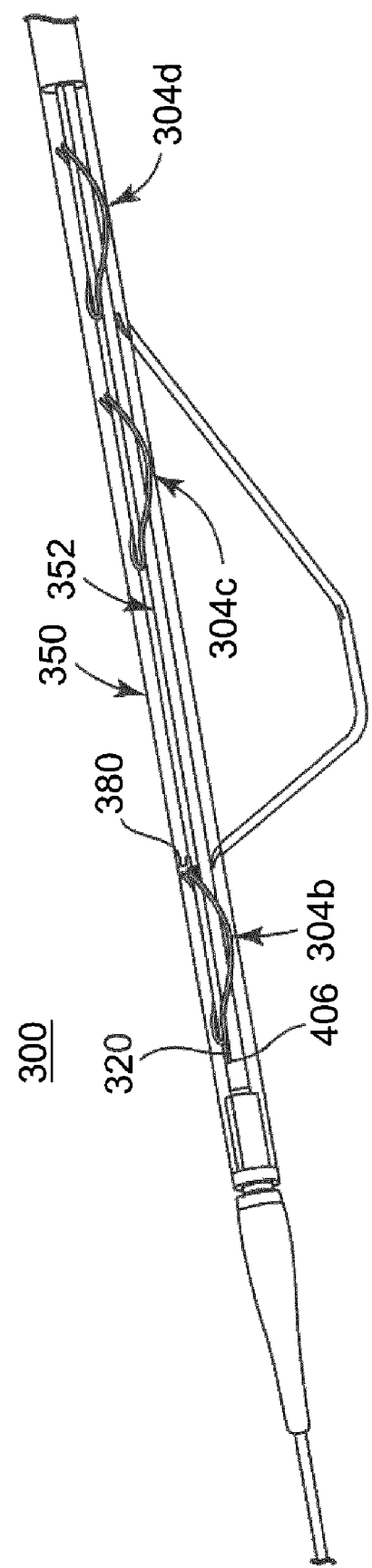

Once the bridge 320 of the second clip 304b has been partially captured by the notch 406, deployment of the second clip 304b can be achieved in an identical manner to that described above with respect to the first clip 304a. In general terms, then, the deployment rod 352 is distally advanced until the distal end 400 contacts the stop member 354 as shown in FIG. 20H. Subsequent, proximal retraction of the deployment rod 352 allows the clip 304b to deploy from the deployment window 380. Loading and deployment of the third and fourth clips 304c, 304d is achieved in a similar manner. In each instance, the clips 304b-304d can be partially deployed and withdrawn/retracted as desired.

The stapling apparatus 300 can be employed in securing an endovascular graft to a vessel wall of a body lumen as described above with respect to FIG. 10. Following delivery of the loaded instrument 302 via the vascular tree of the patient to a target site, the deployment window 380 is arranged as desired, and the optional biasing device 312 (FIG. 12) deployed. Partial deployment and retraction of the first clip 304a and, if deemed necessary, repositioning of the deployment window 380, occurs until the deployment window 380 is optimally positioned relative to the target site and the first clip 304a is then fully deployed. Remaining ones of the clips 304b-304d are subsequently deployed as desired.

The endovascular stapling apparatus of the present disclosure provides a marked improvement over previous designs. One or more staples or clips are endovascularly delivered in a minimally invasive manner, with the treating clinician afforded the ability to achieve optimal placement of the clip(s) by repeatedly partially deploying and retracting each of the clips as desired.

Although the present disclosure has been described with reference to preferred embodiments, workers skilled in the art will recognize that changes can be made in form and detail without departing from the spirit and scope of the present disclosure.

What is claimed is:

1. An endovascular stapling apparatus for delivering a staple to a vessel of a patient, the apparatus comprising:
   a plurality of clips each including a bridge interconnecting opposing legs, the clips being configured to self-transition to a natural state in which the legs each form a loop from a biased state in which the legs are relatively straight as compared to the natural state;
   an elongate housing defining a channel within which the clips are retained in the biased state, the housing forming a deployment window open to the channel; and
   a deployment rod slidably disposed within the channel and configured to interface with the clips;
   wherein the deployment rod is configured to selectively move at least one of the clips toward and away from the deployment window in response to a corresponding user-applied force such that each of the clips are consecutively releasable from the deployment window with movement of the deployment rod.

2. The apparatus of claim 1, wherein the deployment rod includes a distal segment positioned within the housing and a proximal segment extending proximal the housing, the apparatus further comprising:
   an actuator connected to the proximal segment of the deployment rod;
   wherein the device is configured such that a first force imparted upon the actuator causes the deployment rod to move distally relative to the housing, and a second force imparted upon the actuator causes the deployment rod to move proximally relative to the housing.

3. The apparatus of claim 1, further comprising:
a catheter forming a first lumen within which the deployment housing is disposed and forming an exit port open to the first lumen and aligned with the deployment window upon final assembly.

4. The apparatus of claim 3, wherein the catheter further includes a second lumen, the apparatus further comprising:
a guide wire slidably disposed within the second lumen.

5. The apparatus of claim 1, wherein the deployment rod forms a lateral notch defined by a proximal wall and a distal wall, and further wherein a width of the lateral notch between the distal and proximal walls is sized to selectively receive the bridge of one of the clips.

6. The apparatus of claim 5, wherein the distal wall is configured to transfer a pulling force from the deployment rod onto a first side of the corresponding bridge.

7. The apparatus of claim 6, wherein the proximal wall is configured to transfer a pushing force from the deployment rod onto a second side of the corresponding bridge.

8. The apparatus of claim 5, wherein the deployment rod forms a plurality of lateral notches, and further wherein individual ones of the clips are selectively retained within respective ones of the lateral notches.

9. The apparatus of claim 8, wherein upon final assembly of the apparatus, the plurality of lateral notches and the plurality of clips are distal the deployment window.

10. The apparatus of claim 5, wherein the deployment rod defines a shuttle surface proximal the notch and positioned upon final assembly to interface with the bridge of at least one of the clips, the shuttle surface including:
a leading segment adjacent the notch and forming the shuttle surface at a first radial distance relative to a center axis of the deployment rod;
a trailing segment proximal the leading segment and forming the shuttle surface at a second radial distance relative to the center axis, the second distance being less than the first distance; and
a ramp forming a transition of the shuttle surface between the leading and trailing segments.

11. The apparatus of claim 10, wherein with respect to a first clip positioned such that the corresponding bridge is within the notch, the channel is configured to permit movement of the first clip with sliding movement of the deployment rod.

12. The apparatus of claim 11, wherein with respect to a second clip positioned such that the corresponding bridge is along the trailing segment, the channel is configured to retain the second clip in a stationary position with sliding movement of the deployment rod.

13. The apparatus of claim 10, wherein the clips are configured such that when disposed within the channel, the corresponding bridge is radially biased toward the shuttle surface.

14. The apparatus of claim 10, wherein:
an outer surface of the leading segment forms a circle in transverse cross-section; and
an outer surface of the trailing segment forms an incomplete circle in transverse cross-section.

15. The apparatus of claim 10, wherein in an initial, loaded state of the apparatus:
a first one of the clips is positioned such that the corresponding bridge is captured within the notch; and
remaining ones of the clips are positioned such that the corresponding bridges are along the trailing segment.

16. The apparatus of claim 1, further comprising:
a biasing device associated with the housing, the biasing device including a linkage assembly comprising:
a distal link mounted to the housing,
a proximal link slidably connected to the housing, and
at least one intermediate link hingedly connected between the distal and proximal links,
wherein the linkage assembly is configured to radially extend and retract the intermediate link relative to the housing with sliding movement of the proximal link relative to the distal link.

17. An endovascular stapling apparatus for delivering a staple to a vessel of a patient, the apparatus comprising:
a plurality of clips each including a bridge interconnecting opposing legs, the clips being configured to self-transition to a natural state in which the legs each form a loop from a biased state in which the legs are relatively straight as compared to the natural state; and
a delivery instrument comprising:
an actuator,
a delivery assembly including:
a housing forming a channel and a deployment window open to the channel,
a deployment rod slidably disposed within the channel, the deployment rod including a proximal region connected to the actuator,
wherein the channel is sized to constrain the clips to the biased state and the deployment rod is configured to interface with the clips;
a catheter forming a lumen within which at least a portion of the housing is disposed,
an introducer extending distal the housing; and
a guide wire slidably associated with the instrument;
wherein in an initial, loaded state of the apparatus, the actuator is operable to repeatedly move the deployment rod relative to the housing in partially deploying, withdrawing, and fully deploying each of the clips from the deployment window.

18. A method of delivering a staple through a bodily lumen, the method comprising:
providing an endovascular stapling apparatus including:
a plurality of clips each including a bridge interconnecting opposing legs, the clips being configured to self-transition from a biased state in which the legs are relatively straight to a natural state in which the legs each form a loop,
a delivery assembly including:
a housing defining a channel within which the clips are retained in the biased state, and forming a deployment window open to the channel,
a deployment rod slidably disposed within the channel and configured to interface with the clips,
a catheter forming a lumen within which the housing is at least partially disposed;
delivering the delivery assembly into the bodily lumen;
positioning the deployment window at a target site of the bodily lumen;
proximally retracting the deployment rod relative to the housing to deploy a portion of a first clip from the deployment window;
evaluating a position of the partially deployed first clip relative to the bodily lumen;
distally advancing the deployment rod relative to the housing to at least partially withdraw the portion of the first clip back into the housing;
repositioning the delivery assembly relative to the bodily lumen; and proximally retracting the deployment rod relative to the housing to fully deploy the first clip through the deployment window.

19. The method of claim 18, wherein repositioning the delivery assembly relative to the bodily lumen includes the first clip not contacting a structure of the bodily lumen.

20. The method of claim 18, further comprising:
repeatedly, proximally retracting and distally advancing the deployment rod relative to the housing to repeatedly, partially deploy the first clip from, and at least partially withdraw the first clip back into, the deployment window.

21. The method of claim 18, wherein following the step of fully deploying the first clip, the method further comprising:
proximally retracting the deployment rod relative to the housing to deploy a second clip from the deployment window.

22. The method of claim 21, wherein prior to deploying the first clip, the second clip is located distal the deployment window.

23. The method of claim 22, wherein the second clip slides proximally with the deployment rod during the step of proximally retracting the deployment rod to fully deploy the first clip.

24. The method of claim 22, wherein the second clip slides distally with the deployment rod during the step of distally advancing the deployment rod to at least partially withdraw the first clip back into the deployment window.

25. The method of claim 18, wherein following the step of fully deploying the first clip, the method further comprising:
proximally retracting the deployment rod relative to the housing to capture a second clip to the deployment rod;
distally advancing the deployment rod to move at least a portion of the second clip distally beyond the deployment window; and
proximally retracting the deployment rod to deploy the second clip from the deployment window.

26. The method of claim 25, wherein the second clip remains stationary relative to the housing during the step of proximally retracting the deployment rod to fully deploy the first clip.

27. The method of claim 25, wherein the housing and the second clip are configured such that when retained within the housing, the bridge of the second clip is naturally biased against the deployment rod.

28. The method of claim 27, wherein the deployment rod forms a notch for selectively capturing the bridge of the second clip.

29. The method of claim 28, wherein proximally retracting the deployment rod to fully deploy the first clip includes sliding the deployment rod to a first clip deployment position in which the notch is aligned with the deployment window, and further wherein the bridge of the second clip is outside of the notch in the first clip deployment position.

30. The method of claim 29, wherein the bridge of the second clip bears against the deployment rod in the first clip deployment position at a first radial elevation relative to a center axis of the deployment rod and further wherein proximally retracting the deployment rod to capture the second clip includes forcing the bridge of the second rod to a second radial elevation relative to the center axis, the second radial elevation being greater than the first radial elevation.

31. The method of claim 30, wherein forcing the bridge to the second radial elevation includes slidably engaging the bridge of the second clip along a ramp of the deployment rod.

* * * * *